(12) United States Patent
Karczewski et al.

(10) Patent No.: US 9,946,835 B2
(45) Date of Patent: Apr. 17, 2018

(54) METHOD AND SYSTEM FOR THE USE OF BIOMARKERS FOR REGULATORY DYSFUNCTION IN DISEASE

(75) Inventors: Konrad Karczewski, Stanford, CA (US); Michael Snyder, Stanford, CA (US); Atul Butte, Menlo Park, CA (US); Joel T. Dudley, Rye, NY (US); Eurie Hong, Mountain View, CA (US); Alan Boyle, Menlo Park, CA (US); J. Michael Cherry, Stanford, CA (US); Julie Park, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/592,292

(22) Filed: Aug. 22, 2012

(65) Prior Publication Data

US 2013/0116931 A1    May 9, 2013

Related U.S. Application Data

(60) Provisional application No. 61/526,242, filed on Aug. 22, 2011, provisional application No. 61/526,095, filed on Aug. 22, 2011.

(51) Int. Cl.
| | |
|---|---|
| *G06F 19/00* | (2011.01) |
| *G06F 19/24* | (2011.01) |
| *G06F 19/10* | (2011.01) |
| *G06F 19/18* | (2011.01) |

(52) U.S. Cl.
CPC .............. *G06F 19/24* (2013.01); *G06F 19/10* (2013.01); *G06F 19/18* (2013.01)

(58) Field of Classification Search
CPC .. C12N 15/113; C12Q 1/6886; C12Q 1/6883; C12Q 2600/118; G01N 33/57415; G01N 33/57496; G01N 33/5008; G01N 33/502; G01N 33/5067; G01N 33/56966; G01N 33/56988; G01N 33/573; G01N 33/57407
See application file for complete search history.

(56) References Cited

U.S. PATENT DOCUMENTS

| | | | | |
|---|---|---|---|---|
| 8,008,013 | B2 * | 8/2011 | Gaffney et al. | 435/6.11 |
| 8,163,896 | B1 * | 4/2012 | Bentwich | 536/24.5 |
| 2004/0161779 | A1 * | 8/2004 | Gingeras | 435/6 |
| 2012/0059594 | A1 * | 3/2012 | Hatchwell et al. | 702/19 |
| 2013/0116930 | A1 * | 5/2013 | Karczewski et al. | 702/19 |
| 2013/0116931 | A1 | 5/2013 | Karczewski et al. | |
| 2015/0370963 | A9 | 12/2015 | Dewey et al. | |

OTHER PUBLICATIONS

Jürchott, K, et al. PLOS Genetics (Dec. 2010) vol. 6 No. 12 reference No. e1001231.*
Haviv I, Twin Research and Human Genetics (Dec. 2010) vol. 13, No. 6 pp. 643 Abstract No. 1025.*
Boyle et al., "Annotation of functional variation in personal genomes usign RegulomeDB", Genome research 22:1790-1797, 2012.
Candore et al., "Pharmacogenomics: A Tool to Prevent and Cure Coronary Heart Disease", Current Pharmaceutical Design, 2007, vol. 13 pp. 3726-3734.
Chen et al., "-717 A>G polymorphism of human C-reactive protein gene associated with coronary heart disease in ethnic Han Chinese", the Beijing atherosclerosis study Journal of Molecular Medicine vol. 83, 2005, pp. 72-78.
Coop et al., "High-resolution mapping of crossovers reveals extensive variation in fine-scale recombination patterns among humans", Science, vol. 319, 1395-1398, Mar. 7, 2008.
Dewey et al., "Phased Whole-Genome Genetic Risk in a Family Quartet Using a Major Allele Reference Sequence", PLoS Genetics, Sep. 2011, vol. 7, Issue 9, 15 pgs.
Fan et al., "Noninvasive diagnosis of fetal aneuploidy by shotgun sequencing DNA from maternal blood", Proceedings of the National Academy of Sciences USA, Oct. 21, 2008, vol. 105, No. 42, pp. 16266-16271.
Karczewski et al., "Cooperative transcription factor associations discovered using regulatory variation", Proceedings of the National Academy of Science of the United States of America, vol. 108, No. 32, Aug. 9, 2011, pp. 13353-13358.
Shendure et al., "Next-generation DNA sequencing Nature Biotechnology", Nature Biotechnology, Oct. 2008, vol. 26, No. 10, 1135-1145.
Wheeler et al., "The complete genome of an individual by massively parallel DNA sequencing", Nature vol. 452, pp. 872-877, Apr. 17, 2008.
BioPortal, Retrieved from: http://bioportal.bioontology.org/, Printed on Jun. 19, 2017, 3 pgs.
HighWire Press, Wikipedia, Retrieved from: https://en.wikipedia.org/wiki/HighWire_Press, Printed on Jun. 15, 2017, Last modified May 31, 2016, 2 pgs.
Human Genome Variation Society, Database, Retrieved from: www.hgvs.org/dblist/glsdb.html#H, Last updated Mar. 27, 2017, Printed Jun. 15, 2017.
"23andMe", Retrieved from: https://en.wikipedia.org/wiki/23andMe, Last edited: Jun. 14, 2017, Printed: Jun. 19, 2017, 9 pgs.
"A Catalog of Published Genome-Wide Association Studies", Retrieved from: https://web.archive.org/web/20110727063625/http://www.genome.gov/gwastudies/, Jul. 27, 2011, Printed on Jun. 19, 2017.
"A Catalog of Published Genome-Wide Association Studies", Retrieved from: https://www.genome.gov/gwastudies/, Printed on Jun. 19, 2017, Updated on May 12, 2015, 2 pgs.
"Google Scholar Citation Explorer", userscripts.org, Last updated Sep. 15, 2011, Retrieved from: http://userscripts-mirror.org/scripts/show/44965, Printed Jun. 15, 2017, 2 pgs.
"InterMine", Retrieved from: https://en.wikipedia.org/wiki/InterMine, Last edited: May 15, 2017, Printed: Jun. 19, 2017, 3 pgs.
"Pubget", Wkipedia, Retrieved from: https://en.wikipedia.org/wiki/Pubget, Last edited: Feb. 27, 2017, Printed: Jun. 19, 2017, 3 pgs.
"SNPedia", Retrieved from: https://en.wikipedia.org/wiki/SNPedia, Last edited: Sep. 26, 2016, Printed: Jun. 19, 2017, 3 pgs.

(Continued)

*Primary Examiner* — Mary K Zeman
(74) *Attorney, Agent, or Firm* — KPPB LLP

(57) ABSTRACT

Measuring of the binding of a transcription factor (using, for example, chromatin immunoprecipitation) according to the present invention is provides an improved marker for a disease. These markers can be used in diagnostics for diseases where a transcription factor binding event plays a role. Additionally, they can be used to adjust disease risk profiles for healthy individuals as with typical genetic variants.

14 Claims, 9 Drawing Sheets

(56) References Cited

OTHER PUBLICATIONS

"The Cancer Genome Atlas", Retrieved from: https://en.wikipedia.org/wiki/The_Cancer_Genome_Atlas, Last edited: May 1, 2017, Printed: Jun. 19, 2017, 11 pgs.
"The OBO Foundry", Retrieved from: www.obofoundry.org, Printed on Jun. 19, 2017.
Chen et al., "BCL11A represses HBG transcription in K562 cells", Blood Cells Mol Dis, 2009. 42(2): p. 144-9.
Collins et al., "The molecular genetics of human hemoglobin", Prog Nucleic Acid Res Mol Biol, 1984. 31: p. 315-462.
Donlin, "Using the Generic Genome Browser (GBrowse)", Current protocols in bioinformatics I editoral board, Andreas D. Baxevanis . . . [et al.], 2007. Chapter 9, Unit 9.9.
Fullwood et al., "Chromatin interaction analysis using paired-end tag sequencing", Current protocols in molecular biology I edited by Frederick M. Ausubel . . . [et al.], 2010. Chapter 21, Unit 21.15, pp. 1-25.
Green et al., "Charting a course for genomic medicine from base pairs to bedside", National Human Genome Research Institute, Nature, vol. 470, pp. 204-213, Feb. 10, 2011.
Haiqi et al., "Transcriptional regulation of Foxp3 in regulatory T cells", Immunobiology, 216, pp. 678-685, 2010.
Leslie et al., "Non-genomic loss of PTEN function in cancer: not in my genes", Trends Pharmacal Sci, Mar. 2011. 32(3): p. 131-40.
Majewski et al., "The study of eQTL variations by RNA-seq: from SNPs to phenotypes", Trends in Genetics, Feb. 2011. 27(2): p. 72-9.
McCarthy et al., "The CFTR gene and regulation of its expression", Pediatr Pulmonol, 2005. 40(1): p. 1-8, Published online Apr. 1, 2005.
Metherall et al., "Beta zero thalassemia caused by a base substitution that creates an alternative splice acceptor site in an intron", EMBO J, 1986. 5(10): p. 2551-7. PMCID: 1167152.
Ott et al., "Novel regulatory mechanisms for the CFTR gene", Biochem Soc Trans, 2009. 37(Pt 4): p. 843-8. PMCID: 2794656.
Parkinson et al., "Array Express—a public repository for microarray gene expression data at the EBI", Nucleic Acids Res, Jan. 1, 2005. 33(Database issue): p. D553-5. PMCID: 540010.
Rada-Iglesias et al., "A unique chromatin signature uncovers early developmental enhancers in humans", Nature, 2470(7333), Feb. 10, 2011, p. 279-83; doi:10.1038/nature09692.
Rada-Iglesias et al., "Butyrate mediates decrease of histone acetylation centered on transcription start sites and down-regulation of associated genes", Genome Research, 2007. 17(6): p. 708-19.
Reese et al., "Bovine Genome Database: supporting community annotation and analysis of the Bos taurus genome", BMC genomics, Nov. 19, 2010. 11: p. 645. PMCID: 3012608.
Reich et al., "Linkage disequilibrium in the human genome", Nature, vol. 411, May 10, 2001, pp. 199-204.
Robertson et al., "cisRED: a database system for genome-scale computational discovery of regulatory elements", Nucleic Acids Res, Jan. 1, 2006. 34 (Database issue): p. D68-73.
Robinson et al., "The human phenotype ontology", Clin Genet, 2010. 77(6): p. 525-34.
Robinson et al., "The Human Phenotype Ontology: A Tool for Annotating and Analyzing Human Hereditary Disease", The American Journal of Human Genetics, 83, Nov. 7, 2008, pp. 610-615.
Saccone et al., "New tools and methods for direct programmatic access to the dbSNP relational database", Nucleic Acids Res, 39 (Database issue), 2011, p. D901-D907; doi:10.1093/nar/gkq1054, Published online Oct. 29, 2010.
Sargent et al., "The roles of 5'-HS2, 5'-HS3, and the gamma-globin TATA, CACCC, and stage selector elements in suppression of beta-globin expression in early development", J Biol Chem, Apr. 16, 1999. 274(16): p. 11229-36.
Sayers et al., "Database resources of the National Center for Biotechnology Information", Nucleic Acids Research, 39 (Database issue), 2011, p. D38-51;doi:10.1093/nar/gkq1172, Published online Nov. 20, 2010.
Seal et al., "Genenames.org: the HGNC resources in 2011", Nucleic Acids Research, 39 (Database issue), 2011, p. D514-519, Published online Oct. 6, 2010.
Searles, "Transcriptional and posttranscriptional regulation of endothelial nitric oxide synthase expression", Am J Physiol Cell Physiol, 2006. 291(5): p. C803-16, First Published May 31, 2005.
Sherry et al., "dbSNP: the NCBI database of genetic variation", Nucleic Acids Research, Jan. 1, 2001. 29(1): p. 308-11. PMCID: 29783.
Shimada et al., "VarySysDB: a human genetic polymorphism database based on all H-InvDB transcripts", Nucleic Acids Res, 2009. 37(Database issue): p. D810-D815; doi:10.1093/nar/gkn798, Published online Oct. 25, 2008.
Siepel et al., "Evolutionarily conserved elements in vertebrate, insect, worm, and yeast genomes", Genome Research, 2005, 15(8): p. 1034-50, Published online Jul. 2005.
Smith et al., "The OBO Foundry: coordinated evolution of ontologies to support biomedical data integration", Nat Biotechnol, Nov. 2007. 25(11): p. 1251-1255; doi:10.1038/nbt1346.
Stehr et al., "PDBWiki: added value through community annotation of the Protein Data Bank", Database: the journal of biological databases and curation, 2010. 2010: p. baq009, 8 pgs.
Teo et al., "Singapore Genome Variation Project: a haplotype map of three Southeast Asian populations", Genome Research, 2009. 19(11): p. 2154-2162.
Thorisson et al., "HGVbaseG2P: a central genetic association database", Nucleic Acids Research, 2009. 37(Database issue): pp. D797-D802, Published Online Oct. 23, 2008.
Uniprot, "The Universal Protein Resource (UniProt) in 2010", Nucleic Acids Res, 2010. 38(Database issue): p. D142-D148, Published Online Oct. 20, 2009.
Vaquerizas et al., "A census of human transcription factors: function, expression and evolution", Nat Rev Genet, Apr. 2009. 10(4): p. 252-263.
Visel et al., "ChIP-seq accurately predicts tissue-specific activity of enhancers", Nature, Feb. 12, 2009. 457(7231): p. 854-858.
Visel et al., "Genomic views of distant-acting enhancers", Nature, Sep. 2009. 461(7261): p. 199-205; doi:10.1038/nature08451, Manuscript available in PMC Aug. 17, 2010.
Wang et al., "ANNOVAR: functional annotation of genetic variants from high-throughput sequencing data", Nucleic Acids Res, 2010. 38(16): p. e164, 7 pgs, Published online Jul. 3, 2010.
Witkos et al., "Practical Aspects of microRNA Target Prediction", Curr Mol Med, 2011. 11(2): p. 93-109.
Woolfe et al., "CONDOR: a database resource of developmentally associated conserved non-coding elements", BMC Dev Biol, Aug. 30, 2007. 7, 11 pgs.
Woolfe et al., "Highly conserved non-coding sequences are associated with vertebrate development", PLoS biology, Jan. 2005. 3(1): p. e7, 116-130.
Worthey et al., "Making a definitive diagnosis: Successful clinical application of whole exome sequencing in a child with intractable inflammatory bowel disease", Genet Med, Mar. 2011. 13(3): p. 255-62.
Wu et al., "BioGPS: an extensible and customizable portal for querying and organizing gene annotation resources", Genome biology, Nov. 17, 2009. 10(11): p. R130, 8 pgs.
Xu et al., "A comprehensive ChiP-chip analysis ofE2F1, E2F4, and E2F6 in normal and tumor cells reveals interchangeable roles of E2F family members", Genome Research, 2007. 17(11): p. 1550-1561.
Zheng et al., "Regulatory Variation Within and Between Species", Annual Review of Genomics and Human Genetics, vol. 12, Sep. 2011, pp. 327-346, First Published as a Review in Advance on Jul. 1, 2011.
"Definition of Clinical by Merriam-Webster", Retrieved from: https://www.merriam-webster.com/dictionary/clinical, Printed on Jun. 5, 2017, 4 pgs.
"Human genome: Genomes by the thousand", Nature, 467(7319), Oct. 28, 2010, p. 1026-7.
Adzhubei et al., "A method and server for predicting damaging missense mutations", Nat Methods 7(4), Apr. 2010, pp. 248-249.

(56) References Cited

OTHER PUBLICATIONS

Ashley et al., "Clinical assessment incorporating a personal genome", Lancet, May 1, 2010, 375(9725): p. 1525-35, PMCID: 2937184.
Bank, "Regulation of human fetal hemoglobin: new players, new complexities", Blood, 107(2), Jan. 15, 2006, p. 435-43. printed Dec. 5, 2016 from https://www.ncbi.nlm.nih.gov/pmc/articles/PMCID1895603/?report=printable.
Barrell et al., "The GOA database in 2009—an integrated Gene Ontology Annotation resource", Nucleic Acids Research, 2009. 37(Database issue): p. D396-403. PMCID: 2686469.
Bauer et al., "Update on fetal hemoglobin gene regulation in hemoglobinopathies", Curr Opin Pediatr, 23(1), Feb. 2011, p. 1-8.
Beisswanger et al., "Gene Regulation Ontology (GRO): Design Principles and Use Cases", Stud Health Technol Inform, 2008, 136: p. 9-14.
Bejerano et al., "Ultraconserved Elements in the Human Genome", Science, vol. 304(5675), May 28, 2004, p. 1321-1325.
Birney et al., "Identification and analysis of functional elements in 1% of the human genome by the ENCODE pilot project", Nature, vol. 447(7146), Jun. 14, 2007, p. 799-816, PMCID: 2212820.
Blankenberg et al., "Galaxy: a web-based genome analysis tool for experimentalists", Current protocols in molecular, Jan. 2010. Chapter 19: p. Unit 19 10 1-21; doi:10.1002/0471142727.mb1910s89.
Brinkman et al., "Modeling biomedical experimental processes with OBI", J Biomed Semantics, 2010. 1 Suppl1: p. S7. PMCID: 2903726, 11 pgs.
Carver et al., "Artemis and ACT: viewing, annotating and comparing sequences stored in a relational database", Bioinformatics, 2008. 24(23): p. 2672-6. PMCID: 2606163; doi.10.1093/bioinformatics/btn529.
Check, "Human genome at ten: Life is complicated", Nature, vol. 464(7289), Apr. 2010, p. 664-7.
Chen et al., "Non-synonymous and Synonymous Coding SNPs Show Similar Likelihood and Effect Size of Human Disease Association", PLoS ONE, vol. 5, Issue 10, Oct. 22, 2010, e13574-1-e13574-6.
Ciavatta et al., "Mouse model of human beta zero thalassemia: targeted deletion of the mouse beta maj- and beta min-globin genes in embryonic stem cells", Proc. Natl. Acad. Sci. USA, vol. 92, No. 20, Sep. 1995, p. 9259-63.
Consortium, "The Gene Ontology in 2010: extensions and refinements", Nucleic Acids Res, vol. 38 (Database issue), 2010, p. D331-5; doi:10.1093/nar/gkp1018, Published online Nov. 17, 2009.
Consortium et al., "A map of human genome variation from population-scale sequencing", Nature, vol. 467, Oct. 28, 2010, pp. 1061-73; doi:10.1038/nature09534.
Consortium et al., "Integrating common and rare genetic variation in diverse human populations", Nature, 467(7311), Sep. 2, 2010, p. 52-58; doi:10.1038/nature09298.
Cookson et al., "Mapping complex disease traits with global gene expression", Nat Rev Genet, vol. 10, No. 3, Mar. 2009, pp. 184-94; doi:10.1038/nrg2537.
Daub et al., "The RNA WikiProject: community annotation of RNA families", RNA, 2008. 14(12): p. 2462-4.
Ed et al., "Apollo: a community resource for genome annotation editing", Bioinformatics, 25(14), May 2009, pp. 1836-7; doi:10.1093/bioinformatics/btp314.
Edgar et al., "Gene Expression Omnibus: NCBI gene expression and hybridization array data repository", Nucleic Acids Res, 2002. 30(1): p. 207-10.
Elsik et al., "Community annotation: procedures, protocols, and supporting tools", Genome Research, 2006. 16(11): p. 1329-33.
Euskirchen et al., "Mapping of transcription factor binding regions in mammalian cells by ChIP: comparison of array- and sequencing-based technologies", Genome Research, 17(6), 2007, p. 898-909.
Fleming et al., "Molecular mechanisms involved in the regulation of the endothelial nitric oxide synthase", Am J Physiol Regul Integr Comp Physiol, 284(1), 2003, p. R1-12.
Flicek et al., "Ensembl 2011", Nucleic Acids Research, 2011, 39 (Database issue): p. D800-6; doi:10.1093/nar/gkq1064, Published online Nov. 2, 2010.
Fransen et al., "Analysis of SNPs with an effect on gene expression identifies UBE2L3 and BCL3 as potential new risk genes for Crohn's disease", Hum Mol Genet, 19(17), Jul. 2010, p. 3482-8; doi:10.1093/hmg/ddq264.
Fujita et al., "The UCSC Genome Browser database: update 2011", Nucleic Acids Research, 2011. 39 (Database issue): p. D876-82; doi:10.1093/nar/gkq963, Published online Oct. 18, 2010.
Goecks et al., "Galaxy: a comprehensive approach for supporting accessible, reproducible, and transparent computational research in the life sciences", Genome Biology, 2010. 11(8): 13 pgs.; http/genomebiology.com/2010/8/R86.
Griffith et al., "ORegAnno: an open-access community-driven resource for regulatory annotation", Nucleic Acids Research, 2008. 36 (Database issue): p. D107-13; doi:10.1093/nar/gkm967, Published online Nov. 15, 2007.
Harrow et al., "GENCODE: producing a reference annotation for ENCODE", Genome biology, 2006. 7 Suppl1: p. S4 1-9. PMCID: 1810553.
Hernandez-Boussard et al., "The pharmacogenetics and pharmacogenomics knowledge base: accentuating the knowledge", Nucleic Acids Research, 2008, vol. 36 (Database issue), p. D913-8; doi:10.1093/nar/gkm1009, Published Online Nov. 21, 2007.
Hindorff et al., "Potential etiologic and functional implications of genome-wide association loci for human diseases and traits", Proc Natl Acad Sci USA, Jun. 9, 2009. 106(23): p. 9362-7. PMCID: 2687147.
Hirahara et al., "Signal transduction pathways and transcriptional regulation in Th17 cell differentiation", Cytokine Growth Factor Rev, 21(6), Dec. 2010, p. 425-34; doi:10.1016.j.cytogrf.2010.10.006.
Huss et al., "A Gene Wiki for Community Annotation of Gene Function", PLoS biology, 6(7), Jul. 2008, p. e175. PMCID: 2443188.
John et al., "Human MicroRNA targets", PLoS biology, 2(11), Nov. 2004, pp. e363-1-e363-18.
Kasowski et al., "Variation in transcription factor binding among humans", Science, 328(5975), Apr. 2010, p. 232-235; doi:10.1126/science.0083621.
Koch et al., "The landscape of histone modifications across 1% of the human genome in five human cell lines", Genome Research, 2007. 17(6): p. 691-707.
Kozomara et al., "miRBase: integrating microRNA annotation and deep-sequencing data", Nucleic Acids Res, 39 (Database issue), 2011, p. D 152-157; do:10.1093/nar/gkq1027, Published online Oct. 30, 2010.
Krichevsky et al., "MIR-21: a small multi-faceted RNA", Journal of Cellular and Molecular Medicine, 2009. 13(1): p. 39-53.
Kumar et al., "Predicting the effects of coding non-synonymous variants on protein function using the SIFT algorithm", Nat Protoc, 2009. 4(8): p. 1073-82, Published online Jun. 25, 2009.
Kuntzer et al., "Human variation databases", Database, the journal of biological databases and curation, 2010. 2010: p. baq015, 13 pgs.; doi:10.1093/database/baq015.
Lawson et al., "VectorBase: a data resource for invertebrate vector genomics", Nucleic Acids Res, 37(Database issue), 2009, p. D583-587; doi:10.1093/nar/gkn857, Published online Nov. 21, 2008.
Legeai et al., "AphidBase: a centralized bioinformatic resource for annotation of the pea aphid genome", Insect Mol Biol, 19 Suppl 2, Mar. 2010, p. 5-12; doi:10.1111/j.1365-2583.2009.00930.x.
Lewis et al., "Conserved Seed Pairing, Often Flanked by Adenosines, Indicates That Thousands of Human Genes are microRNA Targets", Cell, 120(1), Jan. 14, 2005, p. 15-20.
Lin et al., "Transcription factor binding and modified histones in human bidirectional promoters", Genome Research, 2007. 17(6): p. 818-27, PMCID: 1891341.
Lyne et al., "FlyMine: an integrated database for *Drosophila* and Anopheles genomics", Genome Biology, 8(7):R129, Jul. 5, 2007, 16 pgs.; doi:10.1186/gb-2007—8-7-r129.
Moore et al., "Global analysis of disease-related DNA sequence variation in 10 healthy individuals: Implications for whole genome-

(56) References Cited

OTHER PUBLICATIONS based clinical diagnostics", Genet Med, 13(3), Mar. 2011, p. 210-7; doi.10.1097/GIM.0g013e31820ed321.

Mungall et al., "Evolution of the Sequence Ontology terms and relationships", Journal of biomedical informatics, 2011. 44(1): p. 87-93.

Mungall et al., "Integrating phenotype ontologies across multiple species", Genome biology, 2010. 11(1): p. R2 16 pgs.; http"// genomebioloby.com/2010/11/1/R2.

Natale et al., "The Protein Ontology: a structured representation of protein forms and complexes", Nucleic Acids Res, 39 (Database issue), 2011, pp. D539-D545, Published online Oct. 8, 2010.

Ng et al., "Exome sequencing identifies MLL2 mutations as a cause of Kabuki syndrome", Nat Genet, 42(9), Nov. 2010, p. 790-3. PMCID: 2930028.

Ng et al., "Exome sequencing identifies the cause of a mendelian disorder", Nat Genet, 42(1), Jan. 2010, p. 30-35. PMCID: 2847889.

Nicolae et al., "Trait-Associated SNPs are More Likely to be eQTLs: Annotation to Enhance Discovery from GWAS", PLoS Genet, 6(4), Apr. 2010, pp. e1000888-1-e1000888-10.

Osborne et al., "Annotating the human genome with Disease Ontology", BMC genomics, 10 Suppl1, Apr. 7, 2009, p. S6, 8 pgs.

Pruitt et al., "The consensus coding sequence (CCDS) project: Identifying a common protein-coding gene set for the human and mouse genomes", Genome Research, 2009. 19(7): p. 1316-1323.

Yang et al., "A mouse model for beta 0-thalassemia", Proc Natl Acad Sci USA, vol. 92, Dec. 1995, p. 11608-11612.

\* cited by examiner

METHOD AND SYSTEM FOR THE USE OF BIOMARKERS FOR REGULATORY DYSFUNCTION IN DISEASE

CROSS-REFERENCE TO RELATED APPLICATIONS

This application claims priority to U.S. Provisional Application No. 61/526,242 filed Aug. 22, 2012, which is hereby incorporated by reference in its entirety for all purposes.

This application claims priority to U.S. Provisional Application No. 61/526,095 filed Aug. 22, 2012, which is hereby incorporated by reference in its entirety for all purposes.

GOVERNMENT RIGHTS

This invention was made with Government support under contract HG000237 awarded by the National Institutes of Health. The Government has certain rights in this invention.

BACKGROUND OF THE INVENTION

There have been efforts to describe the regulatory landscape of the human genome using high-throughput or computational methods. Individual labs as well as the ENCODE project, for example, have provided a genome-wide catalogue of DNA elements in the human genome. Shown in FIG. 1 are certain examples of these efforts. Regions that have been identified by high-throughput methods such as ChIP-Seq are sometimes called DNA elements because these sequences have been shown to bind a protein but their effect on gene expression is unknown. For example, as shown in FIG. 1, data type A (reference 152 in FIG. 1) are regulatory regions identified by low-throughput experiments and data type B (154) are DNA elements identified by high-throughput studies.

Among other things, computational analyses of these data have identified patterns of chromatin modification that mark transcriptionally active regions, providing a global view of putative regulatory elements in the human genome. Recent efforts have included the GenotypeTissue Expression (GTEx; www.commonfund.nih.gov/GTEx/) program to identify eQTLs, variations that are associated with changes in gene expression (see FIG. 1, association 118-12 between data types C (polymorphisms 156) and F (expression 162)). Although high-throughput experiments provide broad coverage, the direct mechanism of regulation between these nucleotides and their target gene may not have been identified. The availability of genome sequences of other mammals has identified regions of high conservation in non-protein coding regions, leading to the identification of regulatory regions essential for development (See FIG. 1, data type E (conservation blocks and computational predictions 160). Additionally, computational algorithms can predict regions that are required for gene regulation, such as regions in the 3' UTR that are essential for regulation by microRNAs (see FIG. 1, data type E (conservation blocks and computational predictions 160). These computational datasets can provide hypotheses of functional nucleotides but their biological significance must still be evaluated manually. Shown in FIG. 1 are archetypes of biological data and the current associations between them.

Sequence information, associations between two data types, and a catalog of DNA elements in the human genome alone offer little to scientists and clinicians unless it is associated with functional information. Much of the current knowledge about the role of nucleotides in intergenic and non-coding regions in transcriptional and translational regulation is known through directed experimental studies that are published in peer-reviewed journals. Regions that have been demonstrated to have an effect on protein-nucleic acid interactions, nucleic acid-nucleic acid interactions, or gene expression using mutagenesis and reporter experiments will be referred to as regulatory or functional regions even though their effect on gene function may be limited.

Problematically, it is not easy to identify the relevant literature by searching databases such as PubMed. For example, finding all the papers that identify regulatory regions for the beta-globin locus that contains several developmentally regulated hemoglobin genes or the transcription factor STAT3 in PubMed is not possible with a single query. In February 2011, a search of "beta-globin (with all symbols, names, and aliases) and regulation" of all PubMed records indexed with a "humans" MeSH term retrieved 1334 publications. Only 13% of these papers (177) contain information providing nucleotides or coordinates for regions necessary for repression and activation at the beta-globin locus; the rest discuss post-translational regulation of the proteins required for beta-globin expression. A similar search for STAT3 found 167 out of 1722 papers (9%) that contain information identifying specific nucleotides in STAT3 binding sites or regions that regulated STAT3. Finding and reading these papers on intergenic and non-coding regions is not a feasible task for scientists or clinicians who wish to identify functional nucleotides in hundreds if not thousands of non-coding regions. Even if the papers can be identified, the data cannot easily be integrated in an analysis pipeline.

As sequencing costs drop, full genome sequencing has become possible. Genome sequencing centers predict 30,000 human genome sequences will be available by the end of 2011. But non-coding regions represent 99% of the entire human genome and little is known about many variants already identified in GWAS studies (see FIG. 1, connection 168-3 between data types D (gene function 158) and G (diseases and phenotypes 164)). Analysis and understanding of variation in the human genome has largely focused on protein-coding regions because existing tools and databases have annotated the biological function of genes and their role in biological pathways and disease processes. The Swiss-Prot records at UniProtKB contain annotations of amino acids that are located in the active site or are involved in interactions with other proteins or ligands from the experimental literature. PolyPhen, a widely-used prediction algorithm that identifies deletrious non-synonymous SNPs (nsSNPs), uses these literature-curated data to aid the prediction. Such resources have allowed exome sequencing to become successful as a diagnostic tool to identify genetic causes of rare diseases.

Increased availability of regulatory nucleotides from directed experimental investigations can directly annotate variants identified in GWAS studies and provide biological context to high-throughput and computational datasets, but it can also provide additional information to variants that are in linkage disequilibrium. Therefore, even if the specific SNP identified in a GWAS study has not been studied in the biomedical literature, annotations for regulatory nucleotides in linkage disequilibrium may implicate genes and pathways that contribute to the pathophysiology of disease. In order to accomplish this, regulatory elements in intergenic and non-coding regions must be integrated with high-throughput datasets that describe DNA elements, and regions of sequence variation throughout the genome as well as with annotations that provide functional information and clinical relevance of the genes that are being regulated. In addition, tools and analysis pipelines will need to be developed in order to facilitate the annotation of affected SNPs as well as the identification of relevant SNPs, biological processes, and diseases for results of GWAS studies and whole-genome sequencing.

With the costs of DNA sequencing decreasing, the number of genomes from both healthy and disease tissues is rapidly increasing from the reference genome in 2003, to 16 in 2009, to 50-300 in 2010 to an estimated 30,000 in 2011. A major challenge ahead is to interpret genome sequences and to identify variants responsible for normal and disease phenotypes. At present, most efforts have focused on the identification of changes in protein-coding genes and micro-RNAs (miRNAs) where deleterious alterations can sometimes be deduced. For example, analysis of the Quake genome and, more recently, those of ten other healthy individuals have revealed numerous changes in the protein-coding genes. But most variations from genome sequences as well markers from genome wide association studies (GWAS) identify nucleotide and structural variants that lie outside of coding sequences, and generally these variants are not interpreted. An analysis of dbSNP in March 2011 revealed that approximately 95% of currently known variants are located in non-protein coding regions but fewer than 0.1% have been associated with a publication.

In the last several decades a great deal of information has been generated to analyze regulatory and non-coding sequences in the genome. Initially this information involved analysis of individual genes through mutagenesis, analysis of elements in reporter and/or biochemical assays such as "gel shift" or Chromatin Immunoprecipitation (ChiP). With the advent of genomic approaches, in the past decade, high-throughput studies have been implemented to map regulatory elements on a global scale. These include ChiP-chip (Chromatin immunoprecipitation followed by microarray analyses) or ChiP-Seq (Chromatin immunoprecipitation followed by DNA sequencing) to identify targets throughout the genome and expression quantitative trait loci (eQTL) studies to map potentially regulatory or associated SNPs using changes in expression in a cell or tissue. Currently systematic efforts to collect such information through the ENCODE project have generated approximately 500 ChiP Seq datasets, and this count does not include the significantly large number of datasets generated by individual laboratories not part of the ENCODE project. Presently there is no single resource that houses all of the low-throughput data from individual labs as well as the global data from individual labs as well as consortia. Such a resource would be valuable for the interpretation of variants from large-scale projects such as the HapMap project and Cancer Genome Atlas (www.cancergenome.nih.gov/), as well as the personal genome sequencing efforts going on all around the world, for example.

Therefore, there is a need in the art to associate functional information with non-protein coding variants, so that variants from personal and disease genome sequences as well as GWAS studies can be evaluated by researchers for phenotypic and disease potential.

SUMMARY OF THE INVENTION

An embodiment of the present invention provides biologically meaningful marker for disease than the genetic variants discovered by genetic association studies. These markers more directly test the biological output of a genetic variant that falls in a regulatory (non-protein-coding) region, which are closer to the disease pathology than the initial genetic variant.

Existing methods for disease risk calculations rely on genetic markers that are separated from the biology involved in disease. For diseases where a single protein product is known to be altered in the disease, diagnostics can be done at the protein level, but these are difficult to develop in a high-throughput fashion. But transcription factor binding according to an embodiment of the present invention can be used as an effective, biologically-relevant biomarker that can be rapidly and cost-effectively developed.

Most current risk and/or diagnostics profiles measure genetic or protein variants or levels as the relevant biomarker associated with disease. But genetic variants are conventionally measured without context for the biology they affect. The present invention uses these binding regions as more direct measurements of the molecular phenotype of these variants. Genetic association studies typically identify genetic markers associated with diseases, without necessarily assigning function to the mutations. For example, if these mutations are found in transcription factor binding sites and affect binding of a transcription factor, the actual binding event is likely to be the contributing factor for the disease. Measuring of the binding of a transcription factor (using, for example, chromatin immunoprecipitation) according to the present invention is a better marker for a disease than measuring the genotype. These markers can then be used in diagnostics for diseases where a transcription factor binding event plays a role. Additionally, they can be used to adjust disease risk profiles for healthy individuals, as with typical genetic variants.

Other embodiments of the present invention use other chromatin markers as a biomarker, including modified histones, as well as silencer or represser elements. Genetic markers are only the beginning of a line of biomarkers that confer risk for disease. Typically, these markers can be related to a downstream molecular and physiological effect, of which transcription factor binding can be a key next step. The present invention enables the use of a more biologically impactful biomarker. Other embodiments would be obvious to those of ordinary skill in the art.

An embodiment of the present invention includes a Resource for the Human Regulome as a database for the collection and integration of high-quality experimental results in all nucleotides in intergenic and non-coding regions in the human genome. Among other things, this resource annotates low-throughput and global data concerning regulatory and non-protein coding elements. Using controlled vocabularies, in an embodiment, these experimental results are integrated with (1) trusted datasets that describe the cellular role and clinical relevance of protein-coding and RNA genes, (2) genome-wide association studies that associate sequence variations with diseases, traits, expression profiles, and other phenotypes, (3) regions of sequence conservation, and (4) computational datasets that provide insight into regions that lack experimental investigation. The integration of these data at a Regulome facilitate connecting sequence variation to the genes and biological processes that are regulated by the regions that have been dissected experimentally via linkage disequilibrium provide a resource that can help researchers examine how variations in the entire human genome, and not just the exome, impact biological processes and pathophysiology of disease. In describing embodiments of the present invention, particular reference will be mode to Regulome and RegulomeDB, but it should be understood that such reference does not limit the scope of the present invention.

These and other embodiments can be more fully appreciated upon an understanding of the detailed description of the invention as disclosed below in conjunction with the attached figures.

BRIEF DESCRIPTION OF THE DRAWINGS

The following drawings will be used to more fully describe embodiments of the present invention.

DETAILED DESCRIPTION

Figure 7A:
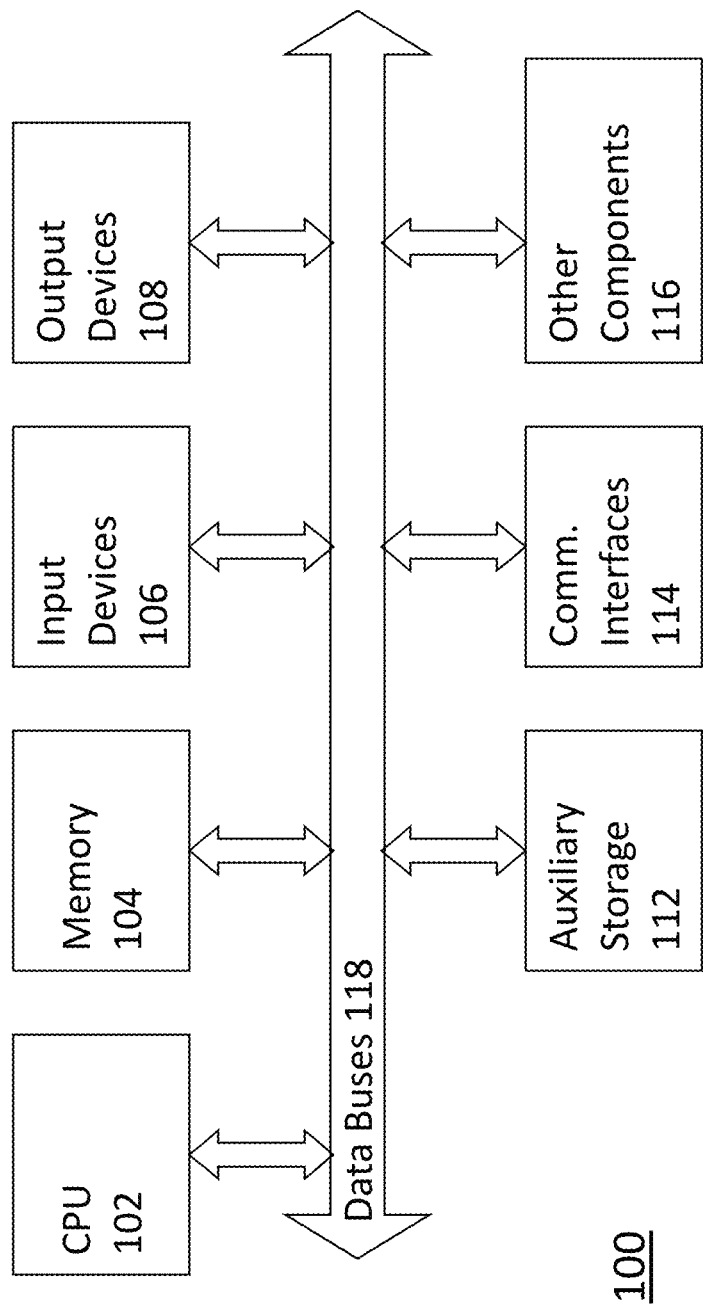
FIGS. 7A and 7B are block diagrams of computer systems on which embodiments of the present invention can be practiced.

Among other things, the present invention relates to methods, techniques, and algorithms that are intended to be implemented in digital computer system 100 such as generally shown in FIG. 7A. Such a digital computer or embedded device is well-known in the art and may include the following.

Computer system 100 may include at least one central processing unit 102 but may include many processors or processing cores. Computer system 100 may further include memory 104 in different forms such as RAM, ROM, hard disk, optical drives, and removable drives that may further include drive controllers and other hardware. Auxiliary storage 112 may also be include that can be similar to memory 104 but may be more remotely incorporated such as in a distributed computer system with distributed memory capabilities.

Computer system 100 may further include at least one output device 108 such as a display unit, video hardware, or other peripherals (e.g., printer). At least one input device 106 may also be included in computer system 100 that may include a pointing device (e.g., mouse), a text input device (e.g., keyboard), or touch screen.

Communications interfaces 114 also form an important aspect of computer system 100 especially where computer system 100 is deployed as a distributed computer system. Computer interfaces 114 may include LAN network adapters, WAN network adapters, wireless interfaces, Bluetooth interfaces, modems and other networking interfaces as currently available and as may be developed in the future.

Computer system 100 may further include other components 116 that may be generally available components as well as specially developed components for implementation of the present invention. Importantly, computer system 100 incorporates various data buses 118 that are intended to allow for communication of the various components of computer system 100. Data buses 118 include, for example, input/output buses and bus controllers.

Indeed, the present invention is not limited to computer system 100 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available.

Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

The present disclosure provides a detailed explanation of the present invention with detailed explanations that allow one of ordinary skill in the art to implement the present invention into a computerized method. Certain of these and other details are not included in the present disclosure so as not to detract from the teachings presented herein but it is understood that one of ordinary skill in the art would be familiar with such details.

Figure 7B:
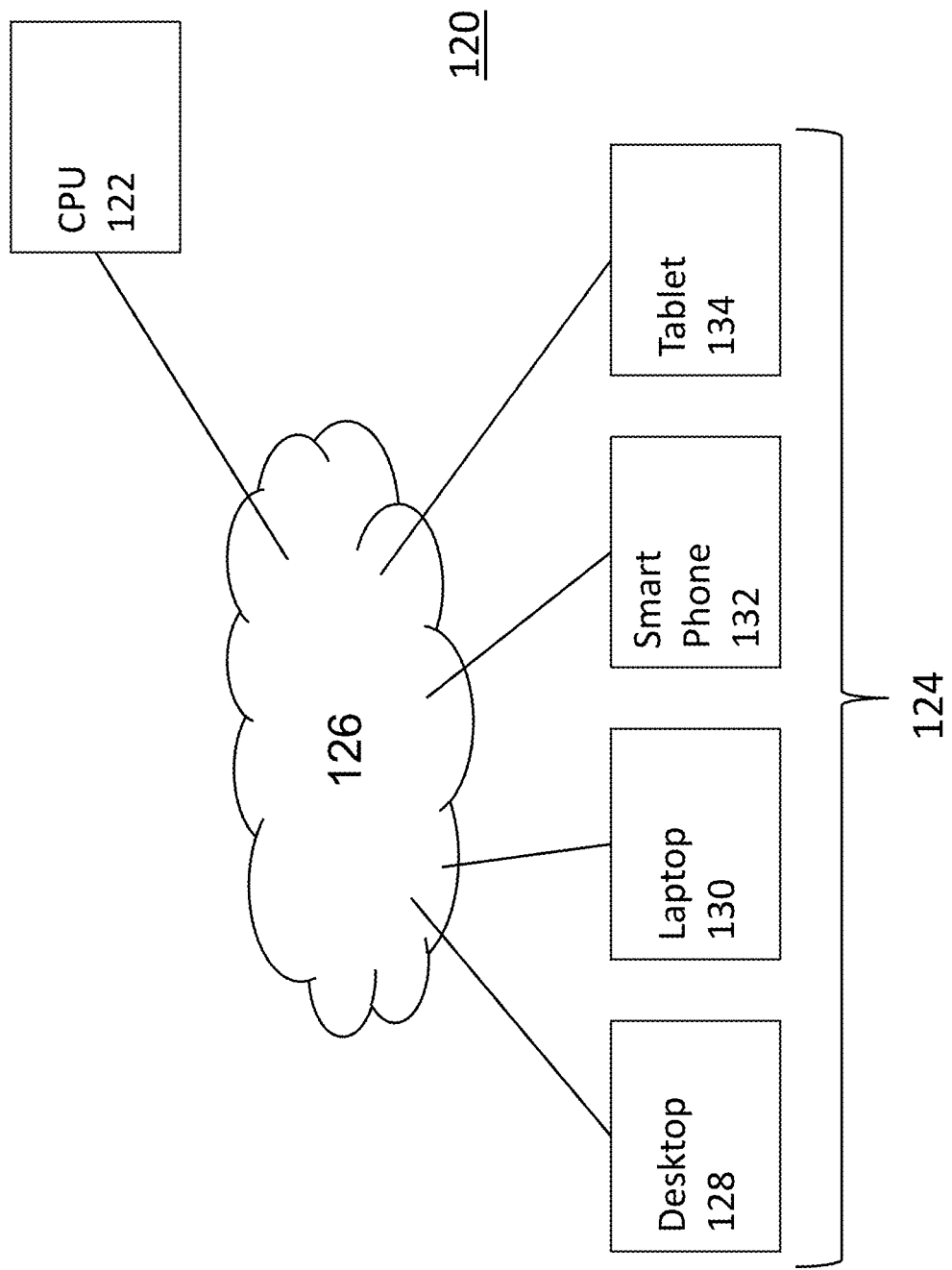

In an embodiment of the invention as shown in FIG. 7B, a computer server that implements certain of the methods of the invention is remotely situated from a user. Computer server 122 is communicatively coupled so as to receive information from a user; likewise, computer server 122 is communicatively coupled so as to send information to a user. In an embodiment of the invention, the user uses user computing device 124 so as to access computer server 122 via network 126. Network 126 can be the internet, a local network, a private network, a public network, or any other appropriate network as may be appropriate to implement the invention as described herein.

User computing device 124 can be implemented in various forms such as desktop computer 128, laptop computer 130, smart phone 132, or tablet device 134. Other devices that may be developed and are capable of the computing actions described herein are also appropriate for use in conjunction with the present invention.

In the present disclosure, computing and other activities will be described as being conducted on either computer server 122 or user computing device 124. It should be understood, however, that many if not all of such activities may be reassigned from one to the other device while keeping within the present teachings. For example, for certain steps computations that may be described as being performed on computer server 122, a different embodiment may have such computations performed on user computing device 124.

In an embodiment of the invention, computer server 122 is implemented as a web server on which Apache HTTP web server software is run. Computer server 122 can also be implemented in other manners such as an Oracle web server (known as Oracle iPlanet Web Server). In an embodiment computer server 122 is a UNIX-based machine but can also be implemented in other forms such as a Windows-based machine. Configured as a web server, computer server 122 is configured to serve web pages over network 126 such as the internet.

In an embodiment, user computing device 124 is configured so as to run web browser software. For example, where user computing device 124 is implemented as desktop computer 128 or laptop computer 130, currently available web browser software includes Internet Explorer, Firefox, and Chrome. Other browser software is available for different applications of user computing device 124. Still other software is expected to be developed in the future that is able to execute certain steps of the present invention.

In an embodiment, user computing device 124, through the use of appropriate software, queries computer server 122. Responsive to such query, computer server 122 provides information so as to display certain graphics and text on user computing device. In an embodiment, the information provided by computer server 122 is in the form of HTML that can be interpreted by and properly displayed on user computing device 124. Computer server 122 may provide other information that can be interpreted on user computing device.

Turning now to a particular discussion of certain embodiments of the present invention, it is noted that it is now possible to determine the genome sequences of large numbers of healthy and disease samples. Although the effect of newly identified variations in protein coding genes may be deduced, the effect of such variations within non-coding regions in the human genome has traditionally been difficult to infer. Embodiments of the present invention, address this and other issues.

Biologically Meaningful Markers:

In an embodiment of the invention, a more biologically meaningful marker for disease than the genetic variants discovered by genetic association studies is used. These markers more directly test the biological output of a genetic variant that falls in a regulatory (non-protein-coding) region, which are closer to the disease pathology than the initial genetic variant. In this embodiment of the invention, transcription factor binding is used as an effective, biologically-relevant biomarker that can be rapidly and cost-effectively developed. The present invention uses these binding regions as more direct measurements of the molecular phenotype of these variants. Genetic association studies typically identify genetic markers associated with diseases, without necessarily assigning function to the mutations, but the present invention does.

According to a method of the invention, if it is determined that these mutations are found in transcription factor binding sites and affect binding of a transcription factor, the actual binding event is determined to be a likely contributing factor for the disease. Measuring of the binding of a transcription factor (using chromatin immunoprecipitation, for example) according to an embodiment of the present invention is found to be a good marker for a disease, for example, when measuring the genotype. These markers can then be used in diagnostics for diseases where a transcription factor binding event plays a role. Additionally, they can be used to adjust disease risk profiles for healthy individuals, as with typical genetic variants.

Figure 8:
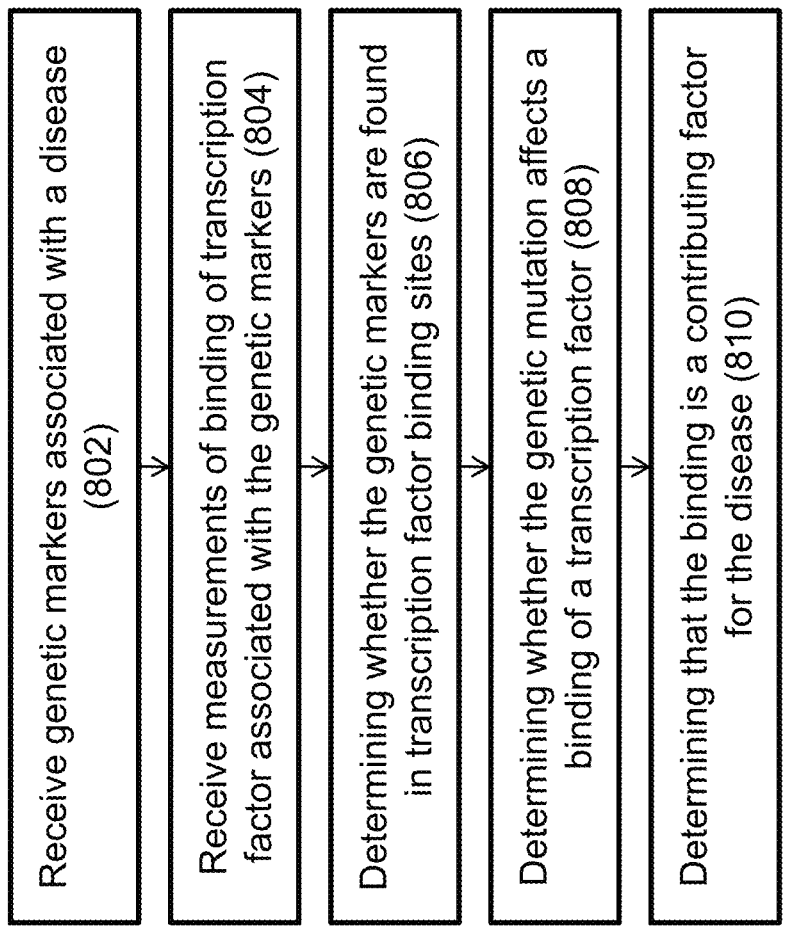
FIG. 8 is a flow diagram of a method according to an embodiment of the present invention.

Shown in FIG. 8 is a method according to an embodiment of the present invention for analyzing genetic variants associated with diseases. As shown at step 802, information is received regarding whether certain genetic markers associated with a disease. At step 804, measurements are received regarding the binding of a transcription factor associated with the genetic markers. In an embodiment, information from chromatin immunoprecipitation is used. Whether the genetic markers are found in transcription factor binding sites is then determined at step 806. At step 808, the method of the present invention determines whether the genetic mutation affects a binding of a transcription factor. If it does, at step 810, it is determined that the binding is a contributing factor for the disease.

The present invention can be expanded to use any chromatin marks as a biomarker, including modified histones, as well as silencer or represser elements. Genetic markers are only the beginning of a line of biomarkers that confer risk for disease. Typically, these markers can be related to a downstream molecular and physiological effect, of which transcription factor binding can be a key next step.

Chromatin Immunoprecipitation (ChIP) is a type of immunoprecipitation experimental technique used to investigate the interaction between proteins and DNA in the cell. It aims to determine whether specific proteins are associated with specific genomic regions, such as transcription factors on promoters or other DNA binding sites, and possibly defining cistromes. ChIP also aims to determine the specific location in the genome that various histone modifications are associated with, indicating the target of the histone modifiers.[1]

Traditionally, to perform, chromatin immunoprecipitation, protein and associated chromatin in a cell lysate are temporarily bonded. The DNA-protein complexes (e.g., chromatin-protein) are then sheared and DNA fragments associated with the proteins of interest are selectively immunoprecipitated. The associated DNA fragments are purified and their sequence is determined. These DNA sequences are generally associated with the protein of interest in vivo.

In the art, there several types of chromatin immunoprecipitation, primarily differing in the starting chromatin preparation. For example, XChIP uses reversibly cross-linked chromatin sheared by sonication called cross-linked ChIP. Native ChIP (NChIP) uses native chromatin sheared by micrococcal nuclease digestion. Embodiments of the present invention can be practiced with either of these or other techniques. Indeed, as other chromatin immunoprecipitation techniques are developed, they can also be used in embodiments of the present invention.

Databases:

An embodiment of the present invention to be described further below is incorporated into a resource for the Human Regulome, which provides an encyclopedia-like collection of gene regulatory elements throughout the human genome. Among other things, the resource provides annotations describing the dissection of DNA elements from directed experimental studies as well as high-throughput datasets, evolutionarily conserved sequence regions, and computational predictions, and powerful tools for the analysis and interpretation of sequence variation. The present invention is a valuable resource for the annotation of non-exonic sequences and to facilitate the interpretation of sequence variations and genetic mutations that contribute to phenotypic variation and human disease.

In an embodiment of the invention, peer-reviewed literature is manually curated for all nucleotides in non-exonic regions that are binding sites or known to regulate gene expression and function in *H. sapiens*. By developing a full-text literature pipeline, an embodiment of the invention annotates all nucleotides in intergenic regions as well as non-coding regions in the *H. sapiens* genome that have been experimentally characterized to regulate transcriptional activity and RNA levels, as well as potential regulatory regions such as transcription factor binding sites, chromatin modifications and DNA methylation sites. This information can then be used, for example, with the method of FIG. 8 according to an embodiment of the present invention. Another embodiment of the present invention uses existing ontologies in order to annotate the type of regulation, the experimental evidence supporting the regulation, the cellular and developmental context used to observe the regulation, and any known associations with diseases.

An embodiment incorporates datasets that provide genomic and cellular context to the regulatory regions that have been defined through directed experiments. Other high-throughput datasets that provide data types similar and complementary to the regulatory elements identified by low-throughput experimental methods as well as datasets that describe the biological function and disease phenotypes of genes, non-coding RNAs, and sequence variants can be incorporated in the present invention. Evolutionary conserved non-coding elements are annotated. Computational predictions, such as targets of regulatory miRNAs and transcription factor binding site motifs, are incorporated to cover regions not yet probed by experimental methods.

In an embodiment, the present invention includes a pipeline method to integrate diverse data types in order to facilitate the association of sequence variations with the regulation of gene expression. The pipeline analyzes all regulatory elements identified in the literature, biochemical elements identified in high-throughput studies, sequence variants, regions of sequence conservation, and computational predictions in order to integrate variation data with biological functions of genes. In an embodiment, these data are used to identify data consistencies in the literature-curated dataset.

Among other things, the present invention provides a resource with tools to annotate variants observed in personal genomes and GWAS studies. The resource can be used to view regions of the *H. sapiens* genome annotated with the integrated results of diverse data types in order to facilitate identifying connections between sequence variation and gene regulation and gene function in *H. sapiens*. The annotation pipeline of an embodiment of the present invention identifies potential changes in gene regulation when variants determined by personal genomics studies and GWAS studies are analyzed. In addition, searches can be performed that allow identification of regulatory sequences shared by a list of genes identified in an experiment or via a query using a biological process or disease.

In an embodiment of the invention, a Resource for the Human Regulome provides a comprehensive, integrated resource of regulatory elements within intergenic and non-coding regions from the published literature, high-throughput datasets, regions of sequence conservation, and computational datasets as well as providing tools for the rapid annotation of variants and identification of biological processes associated with variants identified in personal genome sequences and GWAS studies. In a further embodiment of the present invention, this resource is used to analyze genetic information, including personal genome information.

Data Types

Figure 2:
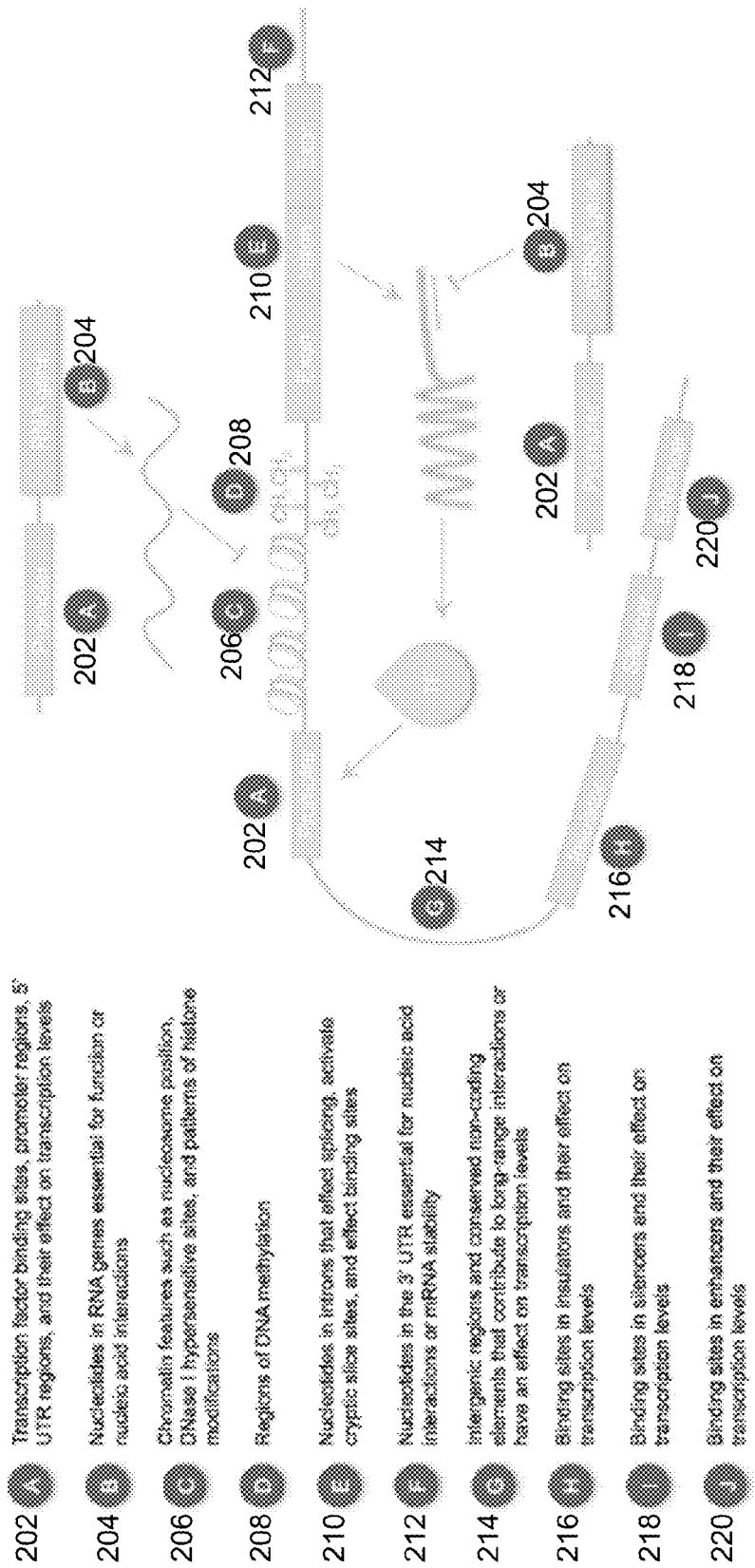
FIG. 2 is a diagram of the various data types that can be curated and integrated according to an embodiment of the present invention.

Among other things, the present invention provides a resource that comprehensively curates all nucleotides in intergenic and non-coding regions in the human genome that have been experimentally characterized in the published literature to regulate RNA or protein levels or binds potential regulatory proteins. Shown in FIG. 2 are various data types 202-220 that can be curated and integrated according to embodiments of the present invention. For example, regions that are considered for curation include intergenic regions, such as transcription factor binding sites, the promoter and 3'-UTR region of genes, insulators, and enhancers, as well as part of non-coding regions, such as introns, miRNAs, and other non-coding RNA genes. Nucleotides in these regions are curated if they have been demonstrated to bind or alter protein-nucleic acid or nucleic acid-nucleic acid interactions, or if an effect on transcription levels of protein-coding genes and non-coding RNAs, levels of transcript stability, gene product levels, or gene product function has been demonstrated.

The present invention identifies and incorporates data types from additional sources similar and complementary to the regulatory elements examined in the low-throughput literature (see, e.g., Table 1). High-throughput studies, created by consortia such as ENCODE and individual labs, provide the similar data types as the low-throughput experiment but on a global scale, for example, and include such data types as nucleosome positions, histone modifications, DNAse I hypersensitive sites, and regions of methylation. Computational datasets can provide insight about transcription factor binding sites or predictions of miRNA targets for regions that have not been probed experimentally. Regions of evolutionary conserved sequence have been shown to be associated with developmental regulators. Comparing computational predictions and regions of sequence conservation against DNA elements studied in low-throughput and high-throughput studies can aid in the interpretation of the functional role of these elements.

Figure 1:
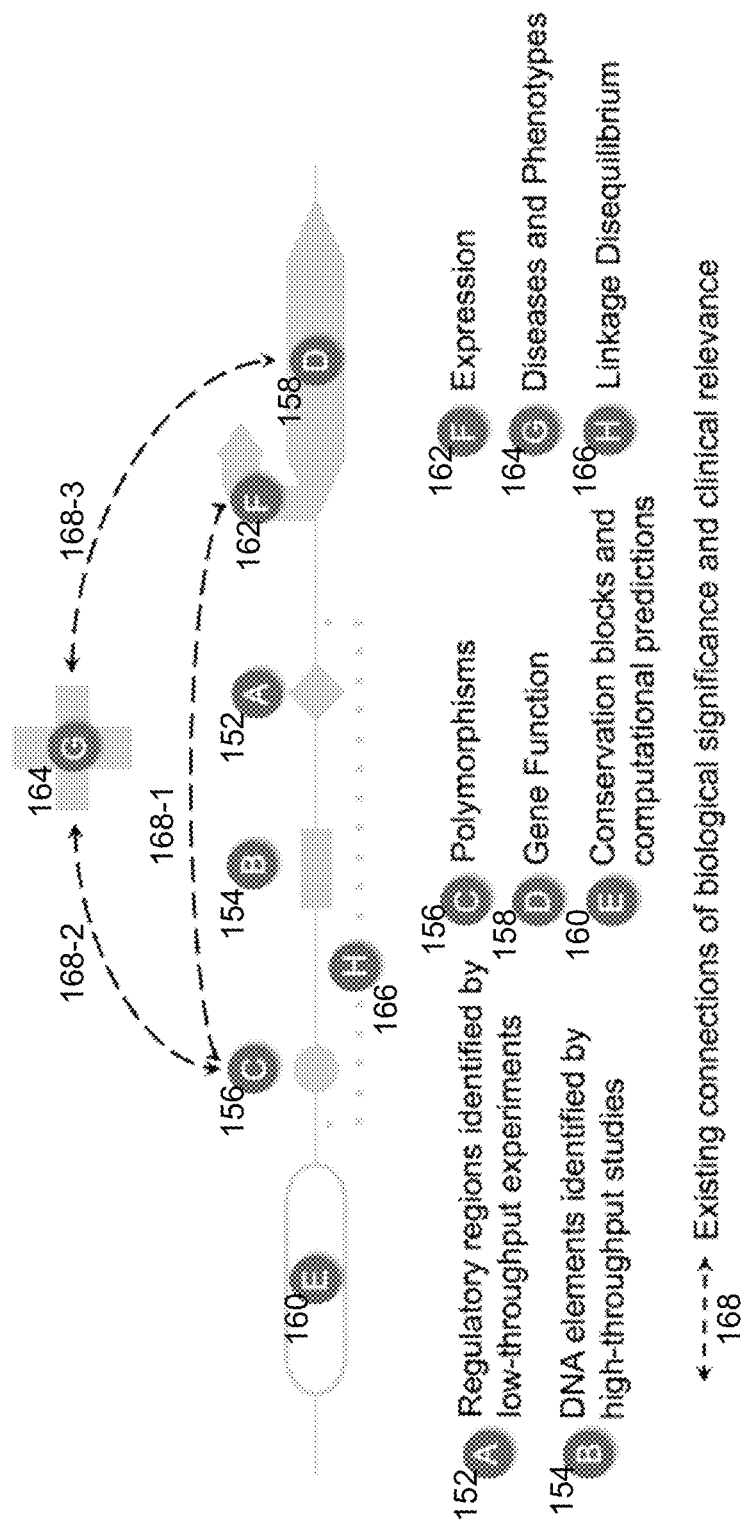
FIG. 1 is a diagram of archetypes of biological data and the conventional associations among them.

Table 1 includes sources of data for the data types available as part of the present invention. The letters refer to the legend in FIG. 1.

TABLE 1

| | A | B | C | D | E | F | G | H | I | J |
|---|---|---|---|---|---|---|---|---|---|---|
| Manual curation of literature | • | • | • | • | • | • | • | • | • | • |
| High-throughput datasets (independent labs and ENCODE) | • | • | • | • | • | • | • | • | • | • |
| Computational predictions | • | • | | | | | • | | | |
| Evolutionarily conserved non-coding elements | • | • | | | | • | | • | | |

Functional Annotations and Clinically Associated Genes and Sequence Variants:

RegulomeDB (the Regulome database according to an embodiment of the present invention) can incorporate the biological function of the genes regulated by the regions that have been examined by directed experimental investigation as well as all associations between these genes and sequence variants with disease. Their inclusion provides the biological context in which connections can be made between sequence variants, gene regulation, and disease phenotypes. Whereas Regulome and RegulomeDB are used to describe certain embodiments of the present invention, they are in now way limiting. Indeed, those of ordinary skill in the art will appreciate that other properly configured databases, for example, can be used in practicing the present invention.

Among other things, the Human Genome Project seeks to understand the biological mechanisms and cellular pathways that contribute to human health and disease risks by sequencing the human genome. An extensive collection of literature-curated databases and analysis tools are available in order to evaluate the functional nucleotides in protein-coding genes, but the resources for nucleotides in intergenic and non-coding regions are limited. In order to provide a more complete view of the role of the sequences in the human genome, the function of regions of the genome must be well annotated. By creating a resource that contains the comprehensive manual curation of regulatory elements in intergenic and non-coding regions, an embodiment of the present invention complements resources such as Entrez Gene, UniProtKB, and locus-specific mutation databases, that focus on functional annotation of protein-coding and RNA genes. These data provide a literature-based dataset of regulatory networks in the human genome and by doing so, are used to help annotate SNPs that are located in these regions that are currently in the public databases, provide a training set for computational and bioinformatic tools, facilitate the annotation of all variations identified in an individual's genome, and provide functional information that can be transferred to conserved non-coding regions from the human genome to other organisms.

An embodiment of the present invention comprehensively curates nucleotides in non-exonic regions that have been experimentally demonstrated to have an effect on gene expression or its interaction with a protein or a nucleic acid. Functional elements in these regions are often identified using mutagenesis and reporter constructs to measure transcription and/or RNA levels of protein-coding and non-coding genes, using electrophoretic mobility shift assays or "gel shifts" to measure transcription factor binding, and measuring the extent of chromatin modification and DNA methylation events. This information can then be used, for example, with the method of FIG. 8 according to an embodiment of the present invention.

Although the effect of these regions on gene expression may not always be measured in a single publication, they will be included for curation because multiple lines of evidence from different publications may provide sufficient support for a regulatory role of that region. In addition to the identification of regulatory nucleotides in intergenic and non-coding regions, the present invention curates nucleotides in these regions that have been shown to be mutated in disease states.

Figure 3:
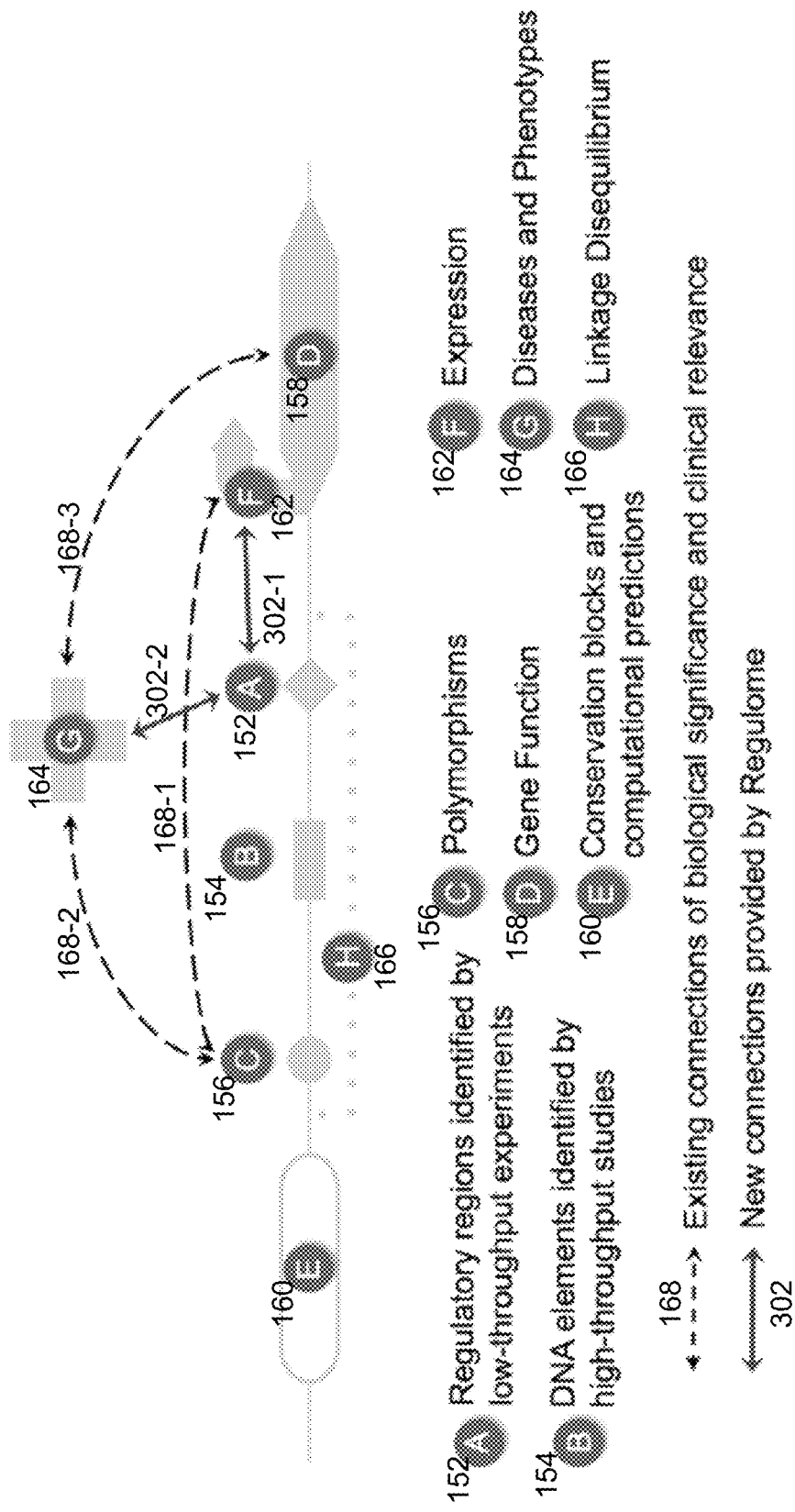
FIG. 3 shows the manner in which an embodiment of the present invention provides associations among intergenic regulatory regions and other biomedical data types.

By maintaining a comprehensive catalog of these regions with supporting experimental evidence, the present invention provides a new connection between experimentally-identified regulatory regions in the human genome with gene expression and disease phenotypes. FIG. 3 shows the manner in which an embodiment of the present invention provides associations between intergenic regulatory regions and other biomedical data types. For example, shown in FIG. 3 is association 302-1 between data types A (152) and G (164) and association 302-2 between data types A (152) and F (162). By connecting experimentally-defined regulatory regions to sequence variants via linkage disequilibrium H (166) as shown in FIG. 3, the present invention provides a valuable resource that allows researchers to identify genes and biological processes for further exploration if their variants map to these genomic regions.

In an embodiment, the nucleotide or range of nucleotides are annotated on the most current *H. sapiens* genome build. The coordinates or sequence are provided in the publication that can be mapped to the current version of the human genome. In an embodiment, all experiments are performed in human tissues or cell cultures with sequences that can be identified in the human genome. Each nucleotide is associated with a description of its function as a biological entity including the gene(s) it regulates, how it regulates the gene(s) or gene product(s), and the experimental evidence supporting the regulation. In an embodiment, the experimental evidence includes the cell line or tissue used for expression studies or a description of the population or cohort studied. If mutational analyses are performed to measure the impact of the intergenic or non-coding region on mRNA or protein expression levels, the reference nucleotide and the mutated nucleotide are captured. Similarly, for variations whose relationship to gene expression or gene function has been examined, the alleles studied and their frequency in the population are also be captured with their regulatory role.

Identification of the Biological Literature:

The priority in literature curation can be publications that contain information about the regulatory role of intergenic and non-protein coding regions and have been characterized to a specific nucleotide region in the human genome. Because biomedical research literature indexed by PubMed can be the source of the literature, but the challenge is to identify a literature search pipeline that will be general enough to cover all these biological processes but provide specificity in the papers that need to be curated [21]. As mentioned earlier, it is difficult to find all papers describing the regions regulating beta-globin or STAT3 expression. The challenges that researchers face in identifying the relevant papers are the same ones encountered here when trying to identify publications that fit within the scope of our curation. As of February 2011, for example, there were 11.5 million papers indexed with a "human" MeSH term. By creating a search that queries each approved HGNC gene symbol, name, and alias as well as a set of non-coding regions (introns OR promoter OR UTR OR miRNA OR insulator OR enhancer OR silencer), the list of results was reduced to approximately 113,000 publications for 21,060 genes and loci in the human genome. Although this search includes several gene and alias names that are non-specific, such as T or PH, or are translated automatically by PubMed into a larger concept, such as GE which becomes "Genetic", these can be removed during the curation process in order to provide a more restricted set of publications for review.

Publications were also required to have "human" as a MeSH term. Although this requires a paper to be indexed by PubMed before it will be retrieved by the automated searches, it excludes references that only mention human in the abstract without addressing the biology of a gene. The list of specific non-coding regions is composed of the regions that will be targeted for curation. These terms may refer either to the cis-regulatory regions of a gene of interest, or to regions that are the targets of the gene product. For example, queries for a transcription factor gene and promoter will identify promoter regions that are targets of the transcription factor as well as promoter regions for its own regulation.

In order to assess the enrichment of relevant publications in the query results, the results for the following genes were reviewed in an embodiment of the present invention: (1) beta-globin locus, a region whose expression has been extensively probed and for which variation in non-coding regions has been associated with disease, (2) CFTR, a tissue-specific gene which causes cystic fibrosis when mutated and whose expression under heterologous promoters has been studied for therapeutic reasons, (3) miR-21, a microRNA with a wide range of targets, (4) PTEN, an oncogene whose regulation has been studied at multiple molecular stages, including processes that involved transcription, mRNA stability, and translation, (4) NOS3, a constitutively expressed gene, and (5) two transcription factors, STAT3 and FOXP3.

The abstracts of the 3600 publications retrieved for these 7 genes were manually screened to identify publications that would not contain information about the regulatory role of nucleotides in intergenic and non-coding regions. Specifically, publications were kept for in-depth curation if the abstract included information that described the key nucleotides required for STAT3, FOXP3, or miR-21 binding to promoter or 5' UTR regions, description of mRNA or protein levels, or identified regions 3' or 5' of the query gene that were essential for its transcription or regulation. This screen suggested approximately 30-65% papers retrieved by the Pubmed search could contain relevant information for RegulomeDB. Following the abstract screening, an in-depth review of the full text of these potentially relevant publications indicated that 20-75% of these papers did contain coordinate information that could be mapped to the current human genome build, and contained data from studies performed in an *H. sapiens* experimental system. Papers describing experiments performed in mammalian systems such as mouse or rat, or in multiple species, were excluded. Papers that did not provide specific coordinates relative to a start site or to a GenBank accession ID were also excluded; examples include description such as 'construct was made with the 1.5 kb promoter region of STAT3'. Results for the transcription factors STAT3 and FOXP3 and the microRNA miR-21 were the most successful, with 30% percent of total publications retrieved from the PubMed query containing curatable information. Results for the constitutively expressed NOS3 were the least productive, resulting in 10% percent of publications retrieved from Pubmed containing curatable information.

Full-Text Based Identification of Data to Curate:

Returning to the PubMed search example, using STAT3 previously discussed, the results from the PubMed query that included specific types of genomic regions improved the retrieval of relevant papers to 35% of all papers reviewed. Although the use of specific regions results in almost a 4-fold improvement in identifying relevant literature compared to "regulation," it still requires review of 605 papers in order to identify the 210 papers that can be curated for STAT3. In order to further reduce the number of papers that need to be manually reviewed for curation, the full texts of these papers were downloaded via PubGet (pubget.com) and Endnote www.endnote.com). For the 7 sample genes surveyed in this preliminary analysis, approximately 90% of all publications have full-text available electronically but only 60-80% are automatically retrievable. In order to achieve a complete corpus of literature for RegulomeDB, PDFs that cannot be downloaded automatically were downloaded manually.

As part of identifying publications that contain experimental information about functional nucleotides, the PDFs are converted into plain text using pdf2text (www.foolabs.com/xpdf/home.html). Of the downloaded PDFs, 95-100% were successfully converted into text, indicating that the rate-limiting step in this process is the acquisition of the PDF. The full text of these articles was searched for word stems "bind" and "muta" in a single paragraph. The pdf2text conversion software keeps paragraphs together as a single line. Therefore, both words did not need to exist in a single sentence. The word stem "bind" was chosen because it can represent DNA binding or RNA binding activities independent of an assay while the word stem "muta" (for mutated or mutant or mutagenesis) indicates that studies were performed to assess whether that nucleotide or region is necessary and sufficient for activity.

Analysis of the results for the 3600 publications indicates that the use of full-text searching results in up to a 4-fold enrichment in the numbers of papers that can be curated. The largest enrichment was seen for NOS3; the full-text search results in 40% of reviewed papers containing curatable data vs the 10% seen when reviewing without the automated filtering step. For the STAT3, FOXP3, miR-21, the addition of the full-text filter resulted in a slight increase in the number of curatable papers compared to the manual review alone, with 40-60% of the papers identified to have curatable information instead of 20-35%.

The advantages to incorporating this method are threefold. First, the number of publications needing manual review decreases. After the full-text search, the number of papers needing manual review dropped to 20-50% of the initial number of papers pulled in. Second, papers containing coordinates that could be mapped to the human genome and experimental evidence on the impact of mutations in non-coding regions represent a higher percentage of the total number of papers. Thirdly, the automated search greatly reduces the amount of time needed to screen publications. For the regulatory genes STAT3, FOXP3, and miR-21, the search was able to identify 70% of the literature that was identified during manual screening alone but in half the time.

Figure 4:
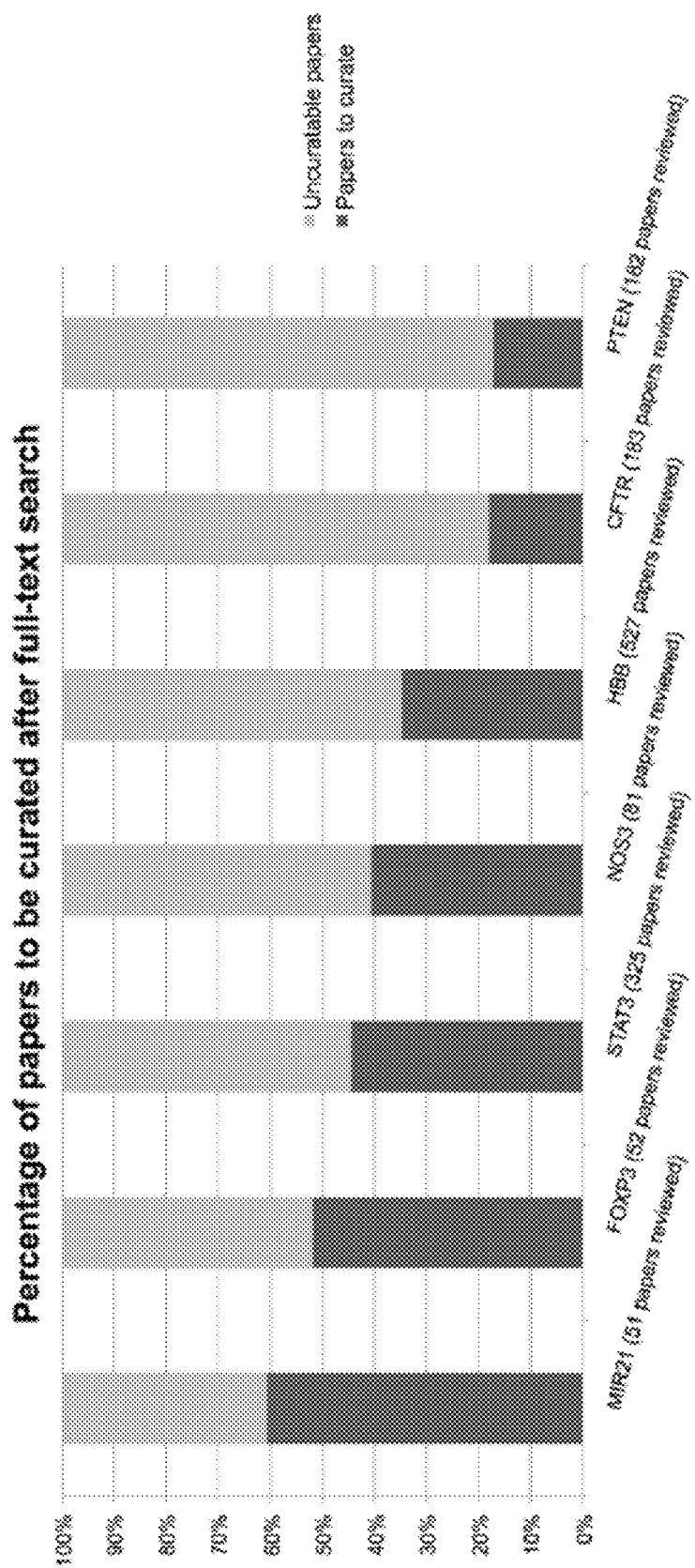
FIG. 4 is a chart that shows the percentage of publications that can be curated after the automated literature pipeline according to an embodiment of the present invention.

FIG. 4 is a chart that shows the percentage of publications that can be curated after the automated literature pipeline. The graph displays the proportion of papers that contain curatable information as determined by comparison to the set of papers identified from the manual in-depth review.

Using Reviews to Ensure Literature Coverage:

Because the pipeline used to identify literature to curate at RegulomeDB according to an embodiment of the present invention is based on a set of genomic locations and involves a full-text search, certain types of papers may be missed. For example, older papers often do not have abstracts in PubMed and may not be identified by the PubMed query. The impact of this on a specific Pubmed search was more significant with genes that have been studied for a long period of time, such as beta-globin.

In addition, due to the variability of natural language, papers that do not contain the phrases used for the Pubmed search in their abstract will be missed. Mutations in an intron may be described as "a mutation in the first intron" or "a mutation in IVS1" or "the mutation activates a cyptic splice site." There is also a nomenclature issue in that the scientific community may not use the HGNC approved symbol, name, or alias. For example, although abstracts describe the function of the miRNA let-7, there is no single miRNA named let-7; there is a let-7 family that contains multiple members. Therefore, the dependence of the PubMed query on HGNC names may result in an underestimate of publications returned for a gene. In the case of let-7, none of the approximately 200 papers describing let-7 were identified by the PubMed query. Additionally, the automated steps in identifying publications to curate will be dependent on the ease of PDF downloading and on whether those PDFs can be converted to text.

Figure 5:
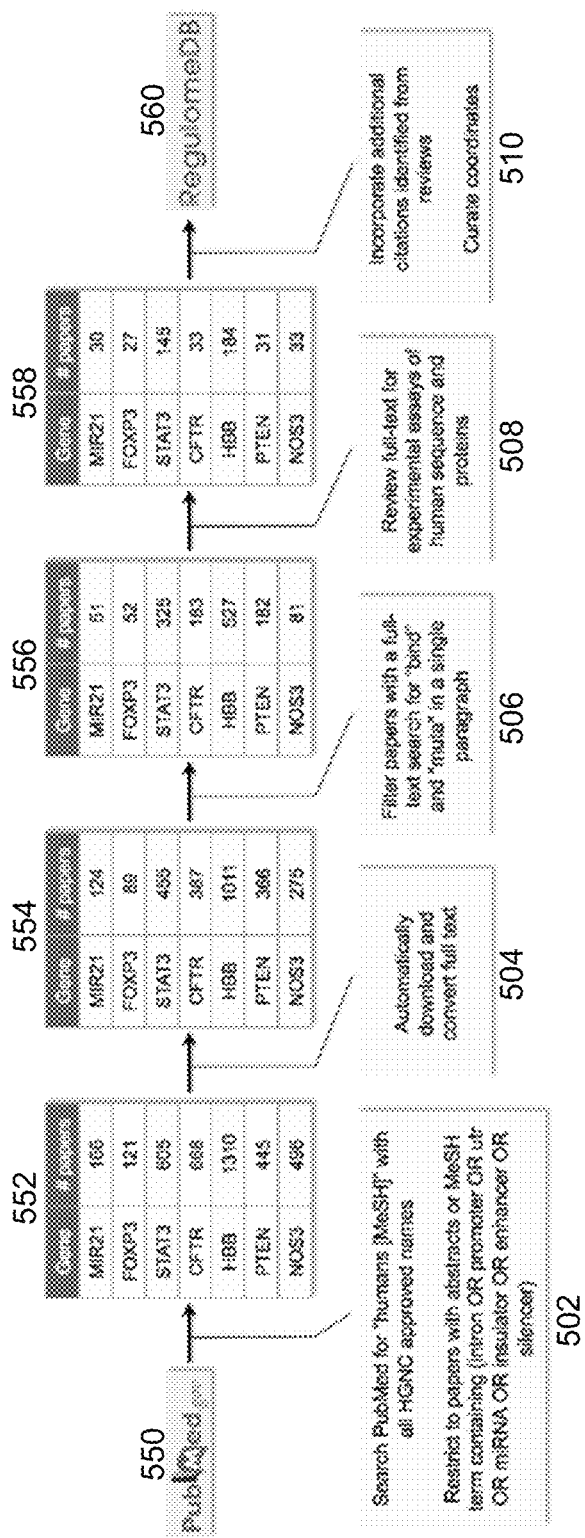
FIG. 5 is a block diagram of a literature pipeline according to an embodiment of the present invention.

To minimize the number of papers that will be missed during the initial curation, several reviews focusing on the regulation of the gene can be used to supplement the PubMed results. Reviews contain a bibliography that has been curated by the authors to best represent the statements made in the publication. Therefore, these bibliopgrahies can be used to ensure that the key publications describing the functional role of intergenic nucleotides are curated. For genes that have been well-studied over several decades, a review can be selected from each decade. This is important because key findings are summarized from the literature regularly and the newer reviews often cite older reviews instead of the primary literature. The integration of these review-identified citations with the automated searching/filtering and manual screening is shown in FIG. 5.

Use of Controlled Vocabularies:

In an embodiment, annotations in RegulomeDB can be captured using controlled vocabularies available in existing biological ontologies or cross-referenced with identifiers used by existing biomedical resources. The ontologies being considered are available from the Open Biological and Biomedical Ontology collaboration (OBO Foundry), which establishes ontological development principles and fosters interoperability for ontologies in the biomedical domain, or the National Center for Biomedical Ontology BioPortal (NCBO; www.bioontology.org, which is a repository of biomedical ontologies).

The types of data captured and examples of ontologies that could be used to capture these entities include: description of the nucleotides using Sequence Ontology (SO); the regulating entity with HGNC or the PRotein Ontology (PRO); the action of regulation via the Gene Regulation Ontology (GRO) or Gene Ontology (GO); experimental methods by the Evidence Code Ontology (ECO; www.obofoundry.org) or the Ontology for Biomedical Investigations (OBI); the cell type or tissue used during experimentation using the Cell Line ontology; diseases and phenotypes associated with the regulated nucleotides using the Disease Ontology (DO) or Human Phenotype Ontology.

In addition to the biological ontologies for basic curation, the use of the Phenotypic Quality Ontology (PATO) can also be implemented to increase the expressivity of the annotations where appropriate. Additional controlled vocabularies and identifiers that can be used or cross-referenced are listed in Table 2. Table 2 shows existing ontologies and classifications that can be used to annotate data in the database of the present invention.

TABLE 2

| Data Types | Potential Controlled Vocabularies |
| --- | --- |
| Sites of Regulation | Sequence Ontology |
| Regulating Gene Products and Complexes | HGNC, Entrez Gene, UniProt, PRotein Ontology |
| Regulatory Process | Gene Regulation Ontology, Gene Ontology |
| Experimental Methods | Evidence Code Ontology, Ontology for Biomedical Investigations Cell Type Ontology, Cell Line Ontology |
| Cell Line/Type | |
| Associated Disease/Trait | Disease Ontology, Human Phenotype Ontology, Systematized Nomenclature of Medicine - Clinical Terms, Unified Medical Language System |
| Population | 1000 Genomes population codes |
| Relationships | OBO Relations Ontology, Phenotypic Quality Ontology |

FIG. 5 is a block diagram of a literature pipeline according to the present invention. At step 502, a search of the database PubMed 550 is performed. As shown, the search was conducted for "humans [MeSH" with all HGNC approved names. The search was restricted to papers with abstracts or MeSH term containing (intron OR promoter OR utr OR miRNA OR insulator OR enhancer OR silencer). Of the found items as shown for in summary table 552, they were automatically downloaded and converted to full text documents at step 504. Shown in summary table 554 are the results of step 504. At step 506, the papers were filtered with a full text search for "bind" and "muta" in a single paragraph. The results of the filtering of step 506 are shown in summary table 556. At step 508, the full text of the documents was reviewed for experimental assays of human sequence and proteins. The results of step 508 are shown in summary table 558. At step 560, additional citations were incorporated as identified by the reviewers. These results were then incorporated into RegulomeDB 560 according to an embodiment of the present invention. In an embodiment, the first three steps (502-506) in the pipeline are automated and performed by scripts. The final two steps (508 and 510) are performed manually in an embodiment but can also be automated.

In addition to using ontologies for literature-based curation, they can also be used to integrate datasets from other genomic resources in an embodiment of the present invention. For example, the diseases listed in the NHGRI GWAS catalog (www.genome.gov/gwastudies) are free-text. These data are mapped to the Disease Ontology when the data are incorporated into the database of the present invention.

The advantages to using these controlled vocabularies are that they provide a framework that allows rigorous computing on the data, an existing infrastructure and community with which to work in further developing these ontologies, and the ability to leverage existing annotations in these resources. For example, by using and linking out on the GO term "positive regulation of mRNA stability," users can see other genes involved in this process in humans as well as those homologous genes that are also involved in mRNA stabilization from the other organisms captured by GO.

Figure 6:
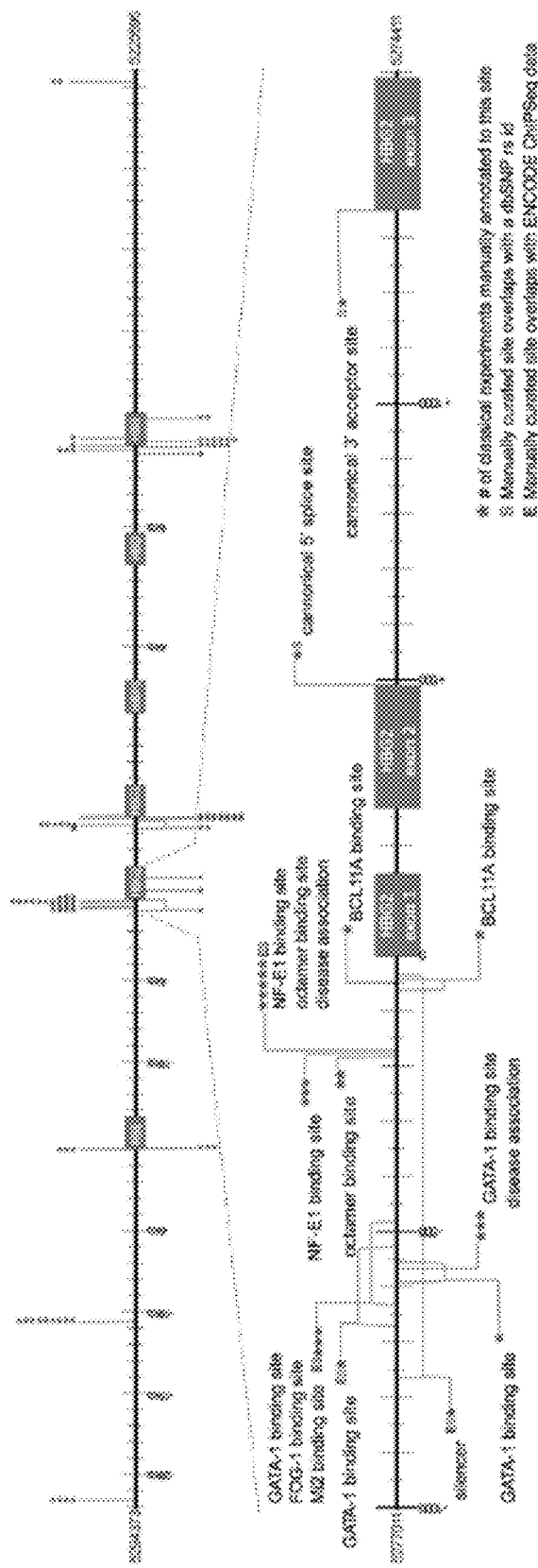
FIG. 6 shows a sample curation of the beta-globin locus according to an embodiment of the present invention.

Preliminary Data Describing the Curation of the Beta-Globin Locus:

In an embodiment of the curation pipeline of the present invention, 25 references identified from reviews and the PubMed query were curated for 88 regions in the beta-globin locus (see FIG. 6). Since 'beta-globin' is an alias of HBB, the PubMed query retrieved papers that addressed the genes in the beta-globin locus, including HBB, HBG1, HBG2, HBD, and HBE. As previously stated, the 1310 references that were retrieved from PubMed were automatically screened in order to identify 184 publications that contained curatable information. An additional 101 papers were identified from reviews. To prioritize the papers for review, the 25 papers that were identified in both the literature pipeline and by reviews were examined first for in-depth curation.

FIG. 6 shows a sample curation of the beta-globin locus. Lines and brackets indicate sites of curated information and stars indicate the number of annotations for that site. Further shown in the upper portion of FIG. 6 is the entire beta-globin region on Chromosome 11 spanning from the 5' to the 3' insulators and in the lower portion is shown a zoomed-in view of the hemoglobin gamma G gene and its upstream regions. The symbols (*, S, E) refer to the evidence score which represents the lines of evidence that support the role of this region having a regulatory role.

During curation, 17 of the 25 publications that were cited by reviews and identified in the literature pipeline could not be used for curation. These publications also highlight some of the difficulties of manual curation of the mammalian literature. Although the sequence examined in these studies were from the human genome, they were studied in a mouse in vivo system, measuring the activity and role of the mouse proteins that regulate expression of the human DNA. Although mice and human pathways of globin regulation are similar, there are key differences, namely that mice do not have gamma-globin genes. Due to this key difference, any admixed experiments were not considered for curation in this embodiment of the present invention. Other embodiments could, however, make use of such information if properly handled.

To provide broad representation of the functional nucleotides in the beta-globin locus, additional publications were reviewed to annotate each functional region with at least one publication. Another 17 papers were curated in order to annotate 88 sites for the five genes in the beta-globin region. Although this represents comprehensive curation of the beta-globin locus exclusively using the literature that investigates the sequences and proteins encoded from the human genome, it does not include regulatory regions such as the FKLF-2, TR2 and TR4, and Ikaros binding sites because those experiments were done in transgenic mice. Examples of these annotations using controlled vocabularies are listed in Table 3. Table 3 shows a sample curation of selected data using controlled vocabularies (see Appendix for more examples).

nates in the reference human genome. Identification of the right sequence to annotate from the experimental literature can involve searching the chromosome with a sequence string that was included in the methods section or calculating a coordinate relative to the transcription start site or translation start site. Once the nucleotide region has been annotated, controlled vocabulary terms need to be assigned to that coordinate. Two open-source genome annotation tools are considered in an embodiment: Artemis, developed by the Sanger Institute, and Apollo, developed and maintained by Berkeley Bioinformatics Open-source Projects group. Both tools accept flat files to view sequence and genome annotation data but can be integrated with the CHADO database. In addition, both tools can be configured to view multiple datasets simultaneously, annotate individual and blocks of nucleotides, and enable the use of multiple ontologies and identifiers when annotating.

Improved Identification of Relevant Literature:

Citations in a publication are a curated source of relevant literature from the scientific community. They are used to

TABLE 3

|  | Sample Annotation 1 | Sample Annotation 2 | Sample Annotation 3 |
| --- | --- | --- | --- |
| Gene | HBG1 (HGNC: 4831) | HBG2 (HGNC: 4832) | HBB (HGNC: 4827) |
| Regulator |  | BCL11A (HGNC: 1322) |  |
| Chromosome | 11 | 11 | 11 |
| Coord Min | 5171112 | 5276062 | 5248044 |
| Coord Max | 5271117 | 5276065 |  |
| Reference nts | ATAAAA | CCGC | T |
| Variant nts | CTGCAG | AAAA | G |
| Feature | TATA box (SO: 0000174) | TF binding site (SO: 0000235) | cryptic splice site acceptor (SO: 0001570) |
| Mutation | substitution (SO: 0001013) | substitution (SO: 0001013) | point mutation (SO: 1000008) |
| Methods | RT-PCR transcription analysis (ECO: 0000108) | EMSA (ECO: 0000096) | RNA protection assay (ECO: 0000110) |
| Cell Line/Type | HEL (MCC: 0000187) | K562 (MCC: 0000261) | reticulocyte (CL: 0000558) |
| Process | mRNA transcription from Pol II promoter (GO: 0042789) | Transcription regulatory region DNA binding (GO: 00442212) | mRNA splicing (GO: 0000398) |
| Disease/Trait |  |  | beta-thalassemia (DOID: 12241) |
| Reference | PMID: 10196210 [45] | PMID: 19153051 [46] | PMID: 3780671 [47] |

The time spent to review the prioritized literature identified via the literature pipeline, identify appropriate papers, and annotate the 25 papers for 88 sites for five genes was approximately 20 hours. This example using the literature pipeline and annotation system demonstrates that the retrieval of papers from the full-text based literature search combined with identification of citations from reviews does provide full coverage of literature in order to comprehensively annotate a very well-studied region of the human genome.

These data were compared to existing resources that could contain regulatory information. The locus-specific mutation database for beta-globin contains a vast number of mutations in the protein-coding sequence but very few in the upstream regulatory region (accessible from www.hgvs.org/dblist/glsdb.html#H). In addition, the literature-curated regulatory database ORegAnno, contains a limited number of regulatory regions and none at nucleotide-level resolution.

Curation Interfaces:

Since the primary curation effort of the present invention is to review the full-text of the paper to identify coordinates, accession numbers, and nucleotides that can be mapped to the human genome, it is essential to have a flexible and functional annotation tool that identifies the correct coordihelp supplement the literature pipeline to identify curatable papers. But to increase efficiency of curation, tools are used that take citations from reviews that discuss regulation of gene function and expression and identify highly cited references that are shared among them. Several online resources can provide information about a relationship between two papers. Google Scholar identifies which papers have cited a single paper while a Mozilla plugin called "Google Scholar Citation Explorer" (compbio.cs.uic.edu/~mayank/software/slh/index.html) will identify papers that have cited a set of selected publications. Web of Science provides information about how often a publication is cited. Highwire (highwire.stanford.edu/) provides citation maps that generates a network of citations from a single paper.

The vast corpus of literature about human biology is a significant challenge. Once a set of literature has been curated for a wide range of genes, text-mining tools can be applied in order to further automate the identification of relevant literature to curate. WormBase has successfully used support vector machine (SVM), a machine learning method, for the targeted identification of literature for curation. SVM creates a classifier from negative and positive training sets by selecting words from each set of publications and constructing a model based on their usage in each of the two sets. The words in a new publication are then applied to the model and scored to determine in which category they fall. The SVM methods developed by WormBase are able to identify similar types of data for *C. elegans*, *D. melanogaster*, and *M. musculus* with high recall (WormBase, personal communication). Once a significant set of papers has been curated to create a positive and negative datasets, text-mining tools such as the SVM methods developed by WormBase can be applied to the uncurated papers in order to prioritize the publications for review.

It has been found that the pipeline can be successful for transcription factors and microRNAs. Even without full-text filtering, approximately 30% of the literature retrieved by PubMed was curatable for miR-21 and STAT3. The automated full-text filter, however, reduced the number of papers that needed to be screened by up to 50% and improved the percentage of papers that contained curatable information (see FIG. 5). In order to get the most breadth of coverage across the genome, it can be efficient and effective to review the literature for the transcription factors and microRNAs followed by highly studied genes.

Based on an analysis performed by Vaquerizas, et al, there are approximately 1500 putative transcription factors in the human genome. Of these, 162 have more than 100 papers identified in the PubMed query using genomic regions as of February 2011. There are approximately 44,000 papers for these transcription factors. Approximately half of the papers for 32 miRNAs with more than 10 papers are already included in the corpus of literature addressing these transcription factors. Therefore, the addition of 500 more papers can cover a total of 162 transcription factors and 32 miRNAs.

The literature can be prioritized so that experiments that describe the functional role of a nucleotide in its ability to interact with a transcription factor or its effect on the metabolism of an RNA transcript or regulation of protein product will be captured first. Although papers that contain data that cannot be mapped back to the current human genome build may not considered for in-depth curation, these publications will remain associated with the regulator, if appropriate, and regulated genes. This will allow researchers access to publications that discuss the regulation of a gene but do not identify specific nucleotides. In addition, papers that identify mutations in intergenic and non-coding regions and are associated with a disease can be curated. As previously mentioned, the full-text literature pipeline may not include certain types of publications. The Amazon Mechanical Turk can be used as a mechanism of community annotation to identify publications that should be curated.

It should be appreciated by those skilled in the art that the specific embodiments disclosed above may be readily utilized as a basis for modifying or designing other techniques for carrying out the same purposes of the present invention. It should also be appreciated by those skilled in the art that such modifications do not depart from the scope of the invention as set forth in the appended claims.

We claim:

1. A computer-implemented method for analyzing genetic variants in transcription factor binding sites, comprising:
   performing a Chromatin Immunoprecipitation-DNA sequencing assay;
   storing the results of the Chromatin Immunoprecipitation-DNA sequencing assay in a first database;
   receiving variant data describing information regarding human genetic variants from the first database and storing the information regarding human genetic variants in memory of a computer system comprising a processor and a memory,
      where the information regarding human genetic variants comprises a genetic variant associated with a disease and a genetic variant coordinate identifying a location on a genetic sequence;
   receiving transcription factor data describing information regarding binding of transcription factor in a human genome and storing the information regarding binding of transcription factor in a human genome on a memory of a computer system comprising a processor and a memory,
      where the information regarding binding of transcription factor in a human genome comprises a transcription factor binding event and a transcription factor binding site, and
      where the transcription factor binding event has been experimentally characterized by a binding intensity indicated by Chromatin immunoprecipitation;
   determining whether the genetic variant coordinate is found within the transcription factor binding site by querying the transcription factor binding site for the genetic variant coordinate, wherein the transcription factor binding site is a regulatory region in the human genome;
   storing the determination whether the genetic variant coordinate is found within the transcription factor binding site on a computer system comprising a processor and a memory;
   determining whether the genetic variant associated with the disease affects the transcription factor binding event based on at least whether the genetic variant coordinate is found within (1) the transcription factor binding site, and (2) the information regarding binding of a transcription factor in a human genome, and (3) the binding intensity of the transcription factor binding event;
   storing the determination whether the genetic variant associated with the disease affects the transcription factor binding event on a computer system comprising a processor and a memory;
   annotating a record of a reference sequence stored in a database of experimental results in intergenic and non-coding regions in the human genome with a functional annotation indicating the human genetic variant at the genetic coordinate according to the determination whether the genetic variant associated with the disease affects the transcription factor binding event, where the functional annotation describes the function of a region of the reference sequence, and a clinical relevance of genes being regulated by the region of the reference sequence;
   obtaining a genetic sequence of a patient;
   querying the database of experimental results in intergenic and non-coding regions in the human genome for records containing functional annotations indicating human genetic variants that are present in the genetic sequence of the patient; and
   taking clinical action by treating the patient in accordance with the clinical relevance described by records containing functional annotations received by the query.

2. The method of claim 1, wherein the functional annotation describes functional elements within the genetic variant associated with the disease and wherein the information regarding binding of transcription factor in a human genome is based on at least a chromatin immunoprecipitation assay.

3. The method of claim 1, wherein the information regarding human genetic variants is received from a database containing text documents describing peer-reviewed scientific studies.

4. The method of claim 1, wherein the variant data includes information from published sources, where published sources comprise peer-reviewed scientific literature and high-throughput datasets, and wherein the method further comprises returning at least one annotated reference sequence from the database in response to a query.

5. The method of claim 1, wherein the transcription factor binding event regulates gene expression in a gene sequence, and wherein the transcription factor binding site is an $NF_\kappa B$ binding region.

6. The method of claim 1, wherein the information regarding human genetic variants is information describing at least a genetic mutation.

7. The method of claim 1, wherein the transcription factor binding event determines a disease risk profile, where the transcription factor binding event is a direct measurement of a molecular phenotype associated with the disease.

8. A computer-implemented method for analyzing genetic variants in transcription factor binding sites, comprising:
performing a Chromatin Immunoprecipitation-DNA sequencing assay;
storing the results of the Chromatin Immunoprecipitation-DNA sequencing assay in a first database;
receiving variant data describing information regarding human genetic variants from the first database and storing the information regarding human genetic variants in a memory,
where the information regarding human genetic variants comprises a genetic variant associated with a disease and a genetic variant coordinate identifying a location on a genetic sequence relative to a transcription start site;
receiving transcription factor data describing information regarding binding of transcription factor in a human genome and storing the information regarding binding of transcription factor in a human genome on a memory,
where the information regarding binding of transcription factor in a human genome comprises a transcription factor binding event and a transcription factor binding site, and
where the transcription factor binding event has been experimentally characterized by a binding intensity indicated by Chromatin immunoprecipitation;
determining whether the genetic variant coordinate is found within the transcription factor binding site by querying the transcription factor binding site for the genetic variant coordinate, wherein the transcription factor binding site is a regulatory region in the human genome;
storing the determination whether the genetic variant coordinate is found within the transcription factor binding site on a memory;
determining whether the genetic variant associated with the disease affects the transcription factor binding event based on at least whether the genetic variant coordinate is found within (1) the transcription factor binding site, and (2) the information regarding binding of a transcription factor in a human genome, and (3) the binding intensity of the transcription factor binding event;
storing the determination whether the genetic variant associated with a disease affects the transcription factor binding event on a memory;
annotating a record of a reference sequence stored in a database of experimental results in intergenic and non-coding regions in the human genome with a functional annotation indicating the human genetic variant at the genetic coordinate according to the determination whether the genetic variant associated with the disease affects the transcription factor binding event, where the functional annotation describes the function of a region of the reference sequence, and a clinical relevance of genes being regulated by the region of the reference sequence;
obtaining a genetic sequence of a patient;
querying the database of experimental results in intergenic and non-coding regions in the human genome for records containing functional annotations indicating human genetic variants that are present in the genetic sequence of the patient; and
taking clinical action by treating the patient in accordance with the clinical relevance described by records containing functional annotations received by the query.

9. The non-transitory computer-readable medium of claim 8, wherein the functional annotation describes functional elements within the genetic variant associated with the disease and wherein the information regarding binding of transcription factor in a human genome is based on at least a chromatin immunoprecipitation assay.

10. The non-transitory computer-readable medium of claim 8, wherein the information regarding human genetic variants is received from a database containing text documents describing peer-reviewed scientific studies, and wherein the method further comprises returning at least one annotated reference sequence from the database in response to a query.

11. The non-transitory computer-readable medium of claim 8, wherein the variant data includes information from published sources, where published sources comprise peer-reviewed scientific literature and high-throughput datasets.

12. The non-transitory computer-readable medium of claim 8, wherein the transcription factor binding event regulates gene expression in a gene sequence, and wherein the transcription factor binding site is an $NF_\kappa B$ binding region.

13. The non-transitory computer-readable medium of claim 8, wherein the information regarding human genetic variants is information describing at least a genetic mutation.

14. The non-transitory computer-readable medium of claim 8, wherein the transcription factor binding event determines a disease risk profile and storing the result on a memory, where the transcription factor binding event is a direct measurement of a molecular phenotype associated with the disease.

* * * * *